(12) United States Patent
Kuwada

(10) Patent No.: US 7,679,747 B2
(45) Date of Patent: Mar. 16, 2010

(54) GLOSS MEASUREMENT APPARATUS AND GLOSS MEASUREMENT METHOD

(75) Inventor: Yoshitaka Kuwada, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 199 days.

(21) Appl. No.: 11/371,160

(22) Filed: Mar. 9, 2006

(65) Prior Publication Data

US 2006/0256341 A1    Nov. 16, 2006

(30) Foreign Application Priority Data

| Mar. 10, 2005 | (JP) | ............................. 2005-067923 |
| Nov. 21, 2005 | (JP) | ............................. 2005-336340 |

(51) Int. Cl.
   *G01N 21/55* (2006.01)
(52) U.S. Cl. .................................................. 356/445
(58) Field of Classification Search ... 356/237.1–237.5, 356/239.7, 445; 250/266, 227
See application file for complete search history.

(56) References Cited

U.S. PATENT DOCUMENTS

| 3,999,864 | A | * | 12/1976 | Mutter ........................ 356/448 |
| 4,806,774 | A | * | 2/1989 | Lin et al. ..................... 250/550 |
| 4,886,355 | A | * | 12/1989 | Keane ........................... 356/73 |
| 4,945,253 | A | * | 7/1990 | Frohardt ................. 250/559.16 |
| 5,153,668 | A | * | 10/1992 | Katzir et al. ............. 356/237.2 |
| 5,428,442 | A | * | 6/1995 | Lin et al. .................. 356/237.5 |
| 5,552,890 | A | * | 9/1996 | Nanna et al. ................ 356/369 |
| 6,166,393 | A | * | 12/2000 | Paul et al. .............. 250/559.08 |
| 6,504,617 | B2 | * | 1/2003 | Komulainen et al. ......... 356/600 |
| 7,336,394 | B2 | * | 2/2008 | Tsujimoto .................... 358/1.9 |
| 2003/0085894 | A1 | * | 5/2003 | Tatsumi ....................... 345/426 |
| 2004/0004731 | A1 | * | 1/2004 | Itagaki ........................ 358/1.9 |
| 2004/0008244 | A1 | * | 1/2004 | Tsujimoto ................... 347/105 |
| 2007/0177233 | A1 | * | 8/2007 | Ichikawa et al. ............ 358/509 |

FOREIGN PATENT DOCUMENTS

| JP | A-05-322764 | | 12/1993 |
| JP | A-11-304703 | | 11/1999 |
| JP | 2002-350355 | | 12/2002 |
| JP | 2002350355 A | * | 12/2002 |
| JP | A-2004-317131 | | 11/2004 |

* cited by examiner

*Primary Examiner*—Tarifur R. Chowdhury
*Assistant Examiner*—Isiaka O Akanbi
(74) *Attorney, Agent, or Firm*—Morgan, Lewis & Bockius LLP

(57) ABSTRACT

A gloss measurement apparatus which emits light from a light source and finds an evaluation value, which represents a glossiness of an object to be measured, on the basis of specular reflected light which is reflected by the object to be measured. The gloss measurement apparatus is provided with an acquisition component, a pixel gloss value calculation component and an evaluation value calculation component. The acquisition component acquires image information in accordance with received light amounts, at predetermined respective pixels, of specular reflected light from a surface of the object to be measured. The pixel gloss value calculation component calculates gloss values of the respective pixels on the basis of the received light amounts at the respective pixels of the image information acquired by the acquisition component. The evaluation value calculation component calculates the evaluation value representing the glossiness of the object to be measured on the basis of the gloss values calculated by the pixel gloss value calculation component.

27 Claims, 20 Drawing Sheets

ORIGIN POINT

GLOSS MEASUREMENT APPARATUS AND GLOSS MEASUREMENT METHOD

CROSS-REFERENCE TO RELATED APPLICATION

This application claims priority under 35 USC 119 from Japanese Patent Applications No. 2005-067923 and No. 2005-336340, the disclosures of which are incorporated by reference herein.

BACKGROUND OF THE INVENTION

1. Field of the Invention

This invention relates to a gloss measurement apparatus and gloss measurement method for emitting light from a light source and, on the basis of specular reflected light which is reflected by an object to be measured, finding an evaluation value which represents a degree of glossiness of the object to be measured.

2. Description of the Related Art

Gloss of a recording medium, and of images and text formed by an image recording device such as a color printer or the like, is a major factor in image quality, which greatly affects the high-quality feel of documents, readability of text and the like, and gloss is utilized as one of the parameters of quality control.

Heretofore, as a method for measuring gloss of a surface of an object, a specular gloss measurement method which projects light onto the surface and measures a reflected light amount in a specular reflection direction to find a degree of gloss value has been widely known (JIS-Z8741). This specular gloss measurement method is a measurement method in which parallel light is incident on an object to be measured at a prescribed incidence angle θ, light flux which has been reflected in the specular reflection direction from the object to be measured is detected by a light detector, and the reflected light flux that has been detected is normalized in accordance with reflected light flux that is detected under the same conditions with a standard surface (a glass surface with a refractive index of 1.567 over the range of visible wavelengths). For this specular gloss measurement method, measurement processes in which 20°, 45°, 60°, 75° and 85° are applied as the incidence angle θ are prescribed. In general, it is considered preferable to use measurement processes in which the incidence angle is small for measurement of objects to be measured with high gloss and measurement processes in which the incidence angle is large for measurement of objects to be measured with low gloss.

However, because the specular gloss value is an index representing a magnitude of reflected light flux in a specular reflection direction, a specular gloss value measured by the above-described specular gloss measurement method might not correspond to a degree of gloss value according to subjective evaluation by human vision (below referred to as subjective glossiness). In such a case, it is not possible to quantitatively find the subjective glossiness from the specular gloss value. Therefore, subjective glossinesses cannot be quantitatively controlled, and problems could arise in control of quality.

SUMMARY OF THE INVENTION

The present invention has been made in view of the above circumstances and provides a gloss measurement apparatus and a gloss measurement method.

A first aspect of the present invention is a gloss measurement apparatus for emitting light from a light source and finding an evaluation value, which represents a glossiness of an object to be measured, on the basis of specular reflected light which is reflected by the object to be measured, the gloss measurement apparatus including: an acquisition component, which acquires image information in accordance with received light amounts, at predetermined respective pixels, of specular reflected light from a surface of the object to be measured; a pixel gloss value calculation component, which calculates gloss values of the respective pixels on the basis of the received light amounts of the respective pixels of the image information acquired by the acquisition component; and an evaluation value calculation component, which calculates the evaluation value representing glossiness of the object to be measured on the basis of the gloss values calculated by the pixel gloss value calculation component.

A second aspect of the present invention is a gloss measurement method for emitting light from a light source and finding an evaluation value, which represents a glossiness of an object to be measured, on the basis of specular reflected light which is reflected by the object to be measured, the method including: acquiring image information in accordance with received light amounts, at predetermined respective pixels, of specular reflected light from a surface of the object to be measured; calculating gloss values of the respective pixels on the basis of the received light amounts of the respective pixels of the acquired image information; and calculating the evaluation value representing gloss value of the object to be measured on the basis of the calculated gloss values.

A third aspect of the present invention is a storage medium readable by a computer, the storage medium storing a gloss measurement program including instructions which are executable by the computer to perform a function for: emitting light from a light source; acquiring image information in accordance with received light amounts, at predetermined respective pixels, of specular reflected light which is reflected by an object to be measured; and finding an evaluation value, which represents a gloss value of the object to be measured, on the basis of the acquired image information, the function including: a pixel gloss value calculation step, for calculating gloss values of the respective pixels on the basis of the received light amounts of the respective pixels of the acquired image information; and an evaluation value calculation step, for calculating the evaluation value representing gloss value of the object to be measured on the basis of the gloss values calculated by the pixel gloss value calculation step.

A fourth aspect of the present invention is a gloss measurement apparatus for emitting light from a light source and finding an evaluation value, which represents a glossiness of an object to be measured, on the basis of specular reflected light which is reflected by the object to be measured, the gloss measurement apparatus including: a specular reflection image information acquisition component, which acquires specular reflected light image information in accordance with received light amounts, at predetermined respective pixels, of specular reflected light from a surface of the object to be measured; and a calculation component, which calculates the evaluation value representing glossiness of the object to be measured on the basis of the specular reflected light image information acquired by the specular reflection image information acquisition component.

A fifth aspect of the present invention is a gloss measurement method for emitting light from a light source and finding an evaluation value, which represents a glossiness of an object to be measured, on the basis of specular reflected light which is reflected by the object to be measured, the method including: acquiring specular reflected light image information in accordance with received light amounts, at predetermined respective pixels, of specular reflected light from a surface of the object to be measured; and calculating the evaluation value representing glossiness of the object to be measured on the basis of the acquired specular reflected light image information.

A sixth aspect of the present invention is a storage medium readable by a computer, the storage medium storing a gloss measurement program including instructions which are executable by the computer to perform a function for emitting light from a light source and finding an evaluation value, which represents a glossiness of an object to be measured, on the basis of specular reflected light which is reflected by the object to be measured, the function including: a storage step, for storing specular reflected light image information at an image information storage component, the specular reflected light image information being acquired in accordance with received light amounts, at predetermined respective pixels, of specular reflected light from a surface of the object to be measured; and an evaluation value calculation step, for calculating the evaluation value representing glossiness of the object to be measured on the basis of the specular reflected light image information which has been stored at the image information storage component.

BRIEF DESCRIPTION OF THE DRAWINGS

Embodiments of the present invention will be described in detail based on the following figures, wherein.

DETAILED DESCRIPTION OF THE INVENTION

Herebelow, embodiments of the present invention will be described in detail with reference to the drawings.

First Embodiment

Figure 1:
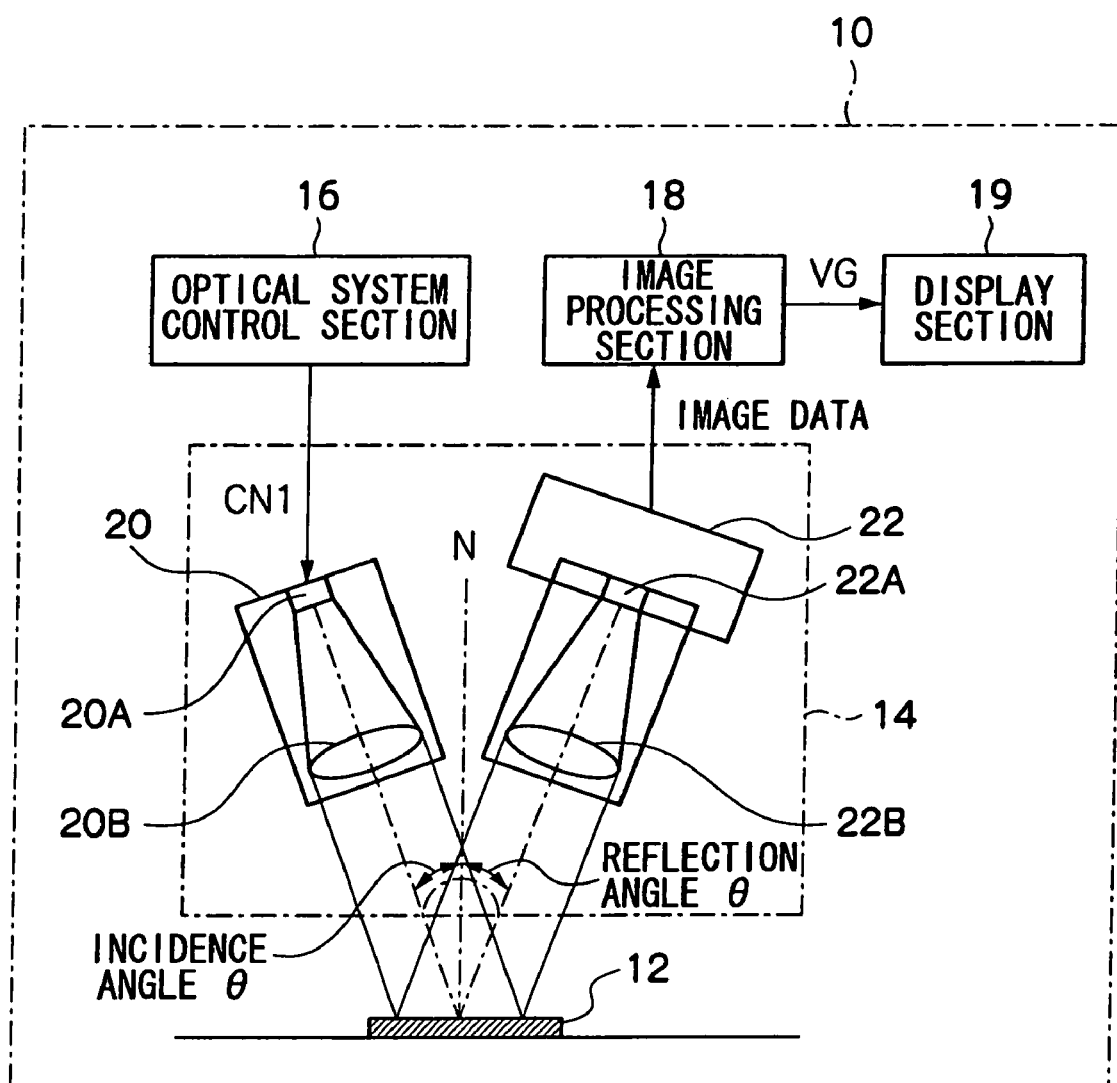
FIG. 1 is a diagram showing schematic structure of a gloss measurement apparatus relating to a first embodiment of the present invention.

FIG. 1 shows general structure of a gloss measurement apparatus 10 relating to the present embodiment.

As shown in FIG. 1, the gloss measurement apparatus 10 is provided with an optics section 14, an optical system control section 16, an image processing section 18 and a display section 19. The optics section 14 emits light onto an object to be measured 12 and performs image capture of specular reflected light from the object to be measured 12. The optical system control section 16 controls operations of the optics section 14. The image processing section 18 performs predetermined image processing on image data (image information) acquired by image capture by the optics section 14, and calculates an evaluation value representing a degree of gloss value of the object to be measured 12. The display section 19 is a liquid crystal display or the like which displays the calculated evaluation value.

The optics section 14 is provided with a light source 20 and an imaging portion 22. The light source 20 emits light onto the object to be measured 12, and the imaging portion 22 captures reflected light that has been reflected by the object to be measured 12.

The light source 20 is disposed at a position from which an optical axis of the light emitted at the object to be measured 12 is incident at a pre-specified incidence angle θ with respect to a normal line N of the object to be measured 12. Meanwhile, the imaging portion 22 is disposed on the optical axis of a direction of specular reflection of the light that is incident on the object to be measured 12 at the incident angle θ (a reflection direction at a reflection angle θ with respect to the normal line N).

The light source 20 is provided with a halogen lamp 20A and a collimator lens 20B. The halogen lamp 20A emits light in accordance with a control signal CN1 which is inputted from the optical system control section 16. The collimator lens 20B is disposed on the optical axis of the light emitted toward the object to be measured 12 from the halogen lamp 20A, and corrects the illumination light to be parallel light. Hence, the parallel light which has been corrected by the collimator lens 20B is emitted at the object to be measured 12. Thus, because the light emitted from the optics section 14 is parallel light, highly accurate detection of gloss nonuniformities is enabled.

The imaging portion 22 is provided with a telecentric lens 22B and a CCD (charge coupled device) area sensor 22A. The telecentric lens 22B focuses the specular reflected light that has been reflected at the object to be measured 12 to a predetermined position. A light-receiving surface of the CCD area sensor 22A is disposed at the focusing position of the telecentric lens 22B. In accordance with received light amounts of the specular reflected light, the CCD area sensor 22A generates image data of each of the colors R (red), G (green) and B (blue), which represents an image of the surface of the object to be measured 12, and outputs the image data to the image processing section 18. Herein, the CCD area sensor 22A relating to the present embodiment has a pixel count of 1392×1040 pixels, a resolution of 11.5 μm and a measurement region of 16×12 mm.

Next, structure of the image processing section 18 relating to the present embodiment will be described in detail with reference to FIG. 2.

Figure 2:
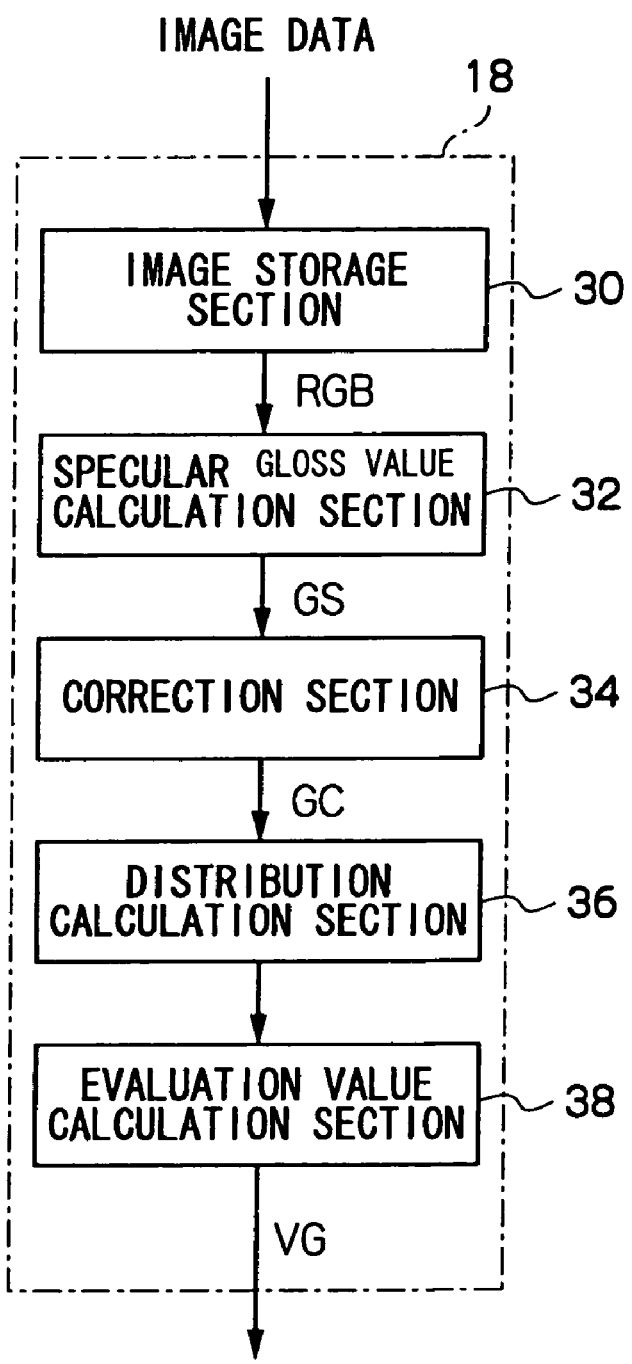
FIG. 2 is a functional block diagram showing detailed structure of an image processing section relating to the first embodiment of the present invention.

As shown in FIG. 2, the image processing section 18 is provided with an image storage section 30, a specular gloss value calculation section 32, a correction section 34, a distribution calculation section 36 and an evaluation value calculation section 38. The image storage section 30 stores image data representing light amounts for each pixel and each of R, G and B, which data is obtained by capture by the imaging portion 22. The specular gloss value calculation section 32 calculates a degree of specular gloss value GS of each pixel of the image represented by the image data, from the R, G and B light amounts of each pixel. The correction section 34 carries out a correction to cause a spatial frequency characteristic of the calculated specular gloss values GS of the pixels to correspond with a spatial frequency characteristic of human vision. The distribution calculation section 36 calculates a distribution of pixel counts for respective gloss values of gloss-corrected values GC which have been corrected by the correction section 34. The evaluation value calculation section 38, on the basis of the distribution calculated by the distribution calculation section 36, calculates an evaluation value which attains a correspondence with subjective glossiness.

Here, the image storage section 30 relating to the present embodiment is structured by a hard disk, but this is not a limitation. The image storage section 30 may be structured by other non-volatile memory, such as flash memory or the like.

If the specular gloss value calculation section 32 relating to the present embodiment represents a two-dimensional co-ordinate position of each pixel of the image represented by the image data with (x,y), and R, G and B light amounts of the pixel (x,y) with R(x,y), G(x,y) and B(x,y), the specular gloss value GS(x,y) of each pixel is calculated using the following equation (1).

$$GS(x,y) = k1 \times R(x,y) + k2 \times G(x,y) + k3 \times B(x,y) \quad (1)$$

Here, for the coefficients k1 to k3 in equation (1), a sample (object to be measured) of which the specular gloss value GS is already known is imaged, and average values (R_ave, G_ave, B_ave) of the light amounts for R, G and B of all pixels are found. Using these average values and the already known specular gloss value GS, optimum values of the coefficients k1 to k3 are preparatorily found by regression analysis of equation (1) and employed.

The specular gloss value calculation section 32 relating to the present embodiment preparatorily stores light amounts R_ref(x,y), G_ref(x,y) and B_ref(x,y) of a standard surface which has been measured beforehand (a black glass surface whose refractive index is 1.567). The specular gloss value calculation section 32 normalizes the light amounts R(x,y), G(x,y) and B(x,y) for each of R, G and B of the respective pixels in accordance with the light amounts R_ref(x,y), G_ref(x,y) and B_ref(x,y).

Next, structure of the correction section 34 relating to the present embodiment will be described in detail with reference to FIG. 3.

Figure 3:
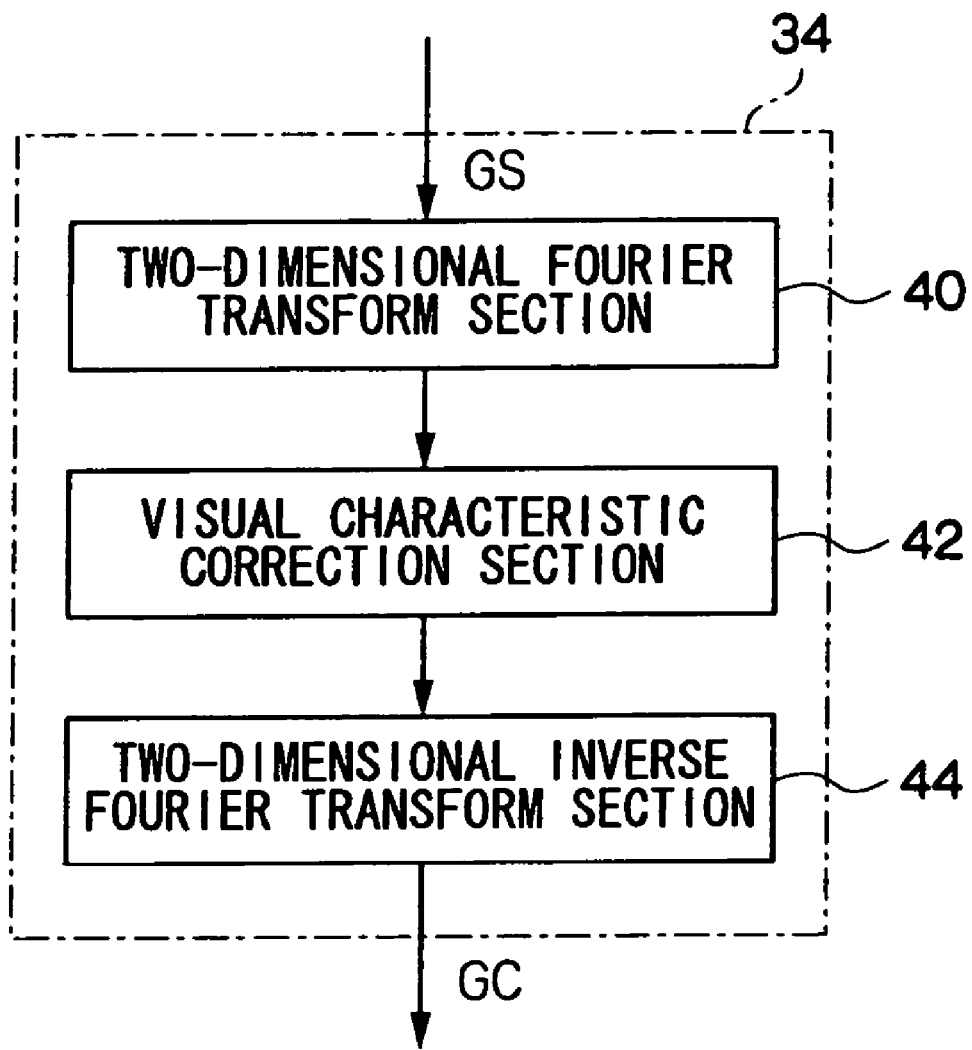
FIG. 3 is a functional block diagram showing detailed structure of a correction section relating to the first embodiment of the present invention.

As is shown in FIG. 3, the correction section 34 is provided with a two-dimensional Fourier transform section 40, a visual characteristic correction section 42 and a two-dimensional inverse Fourier transform section 44. The two-dimensional Fourier transform section 40 converts the specular gloss values GS(x,y) to frequency information F(u,v), which represents specular gloss values in a spatial frequency domain, by performing a two-dimensional Fourier transform on the specular gloss values GS(x,y). The visual characteristic correction section 42 performs a correction to match human visual characteristics, by multiplying a predetermined visual transfer function (VTF), which corresponds to spatial frequency characteristics of human vision and will be described later, with the frequency information F(u,v) which has been converted to the spatial frequency domain by the two-dimensional Fourier transform section 40. The two-dimensional inverse Fourier transform section 44 performs a two-dimensional inverse Fourier transform on the frequency information F(u,v) that has been corrected by the visual characteristic correction section 42, thus converting the frequency information F(u,v) to corrected gloss values GC(x,y) in an image space domain.

Here, the frequency information F(u,v) is converted to polar co-ordinates F(f,θ), and the visual characteristic correction section 42 relating to the present embodiment multiplies the visual transfer function VTF(f) of the following equation (2) therewith for each of values of θ. Although equation (2) is employed as the visual transfer function in the present embodiment, various formulas have been proposed as visual transfer functions, and such formulas may be used.

$$VTF(f) = 5.05 \times [e^{(-0.843 \times f)} - e^{(-1.45 \times f)}] \quad (2)$$

Here, f represents spatial frequency (cycles/degree).

Accordingly, when the visual transfer function VTF(f) is multiplied with the frequency information F(u,v) representing specular gloss values, frequencies for which human visual sensitivity is higher are emphasized, and attaining a correspondence with subjective glossiness is further facilitated.

The distribution calculation section 36 relating to the present embodiment (see FIG. 2) calculates a distribution of pixel counts of each gloss value (see FIG. 9) in the image represented by the gloss-corrected values GC(x,y), on which correction has been performed by the above-described correction section 34 to match human visual characteristics.

Then, the evaluation value calculation section 38 relating to the present embodiment identifies a gloss value A at which, in the distribution of pixel counts for respective gloss values that has been calculated by the distribution calculation section 36, a number of pixels which is a sum of pixel counts for gloss values higher than the gloss value A is a predetermined number (in the present embodiment, half of a total number of pixels). The evaluation value calculation section 38 sums the gloss values of the respective pixels at and above the gloss value A (pixels of the shaded area of FIG. 9) to obtain a total gloss value GM, performs a logarithm transformation of the total gloss value GM, and outputs the logarithm value to the display section 19 (see FIG. 1) to serve as a gloss evaluation value VG.

Next, a flow of operation of the gloss measurement apparatus 10 relating to the present embodiment when measurement of the gloss evaluation value VG of an image recorded at a recording medium is carried out by the gloss measurement apparatus 10 will be described.

The object to be measured 12 is placed at a predetermined position of a portion below the optics section 14 by a user, and predetermined control instructing commencement of measurement of the gloss evaluation value VG is implemented. Then, in the gloss measurement apparatus 10, the control signal CN1 is outputted from the optical system control section 16 to the halogen lamp 20A, the halogen lamp 20A emits light, and the light from the light source 20 is emitted onto the object to be measured 12. Hence, at the imaging portion 22, specular reflected light which has been reflected by the object to be measured 12 is focused on the CCD area sensor 22A and an image is captured, and the captured image data is outputted to the image processing section 18.

At the image processing section 18, the outputted image data is stored at the image storage section 30, gloss evaluation value calculation processing, which will be described later, is carried out on the basis of the stored image data to calculate the gloss evaluation value VG, and the gloss evaluation value VG is outputted to the display section 19.

Thus, a calculated gloss evaluation value VG of the object to be measured 12 is displayed at the display section 19.

Figure 4:
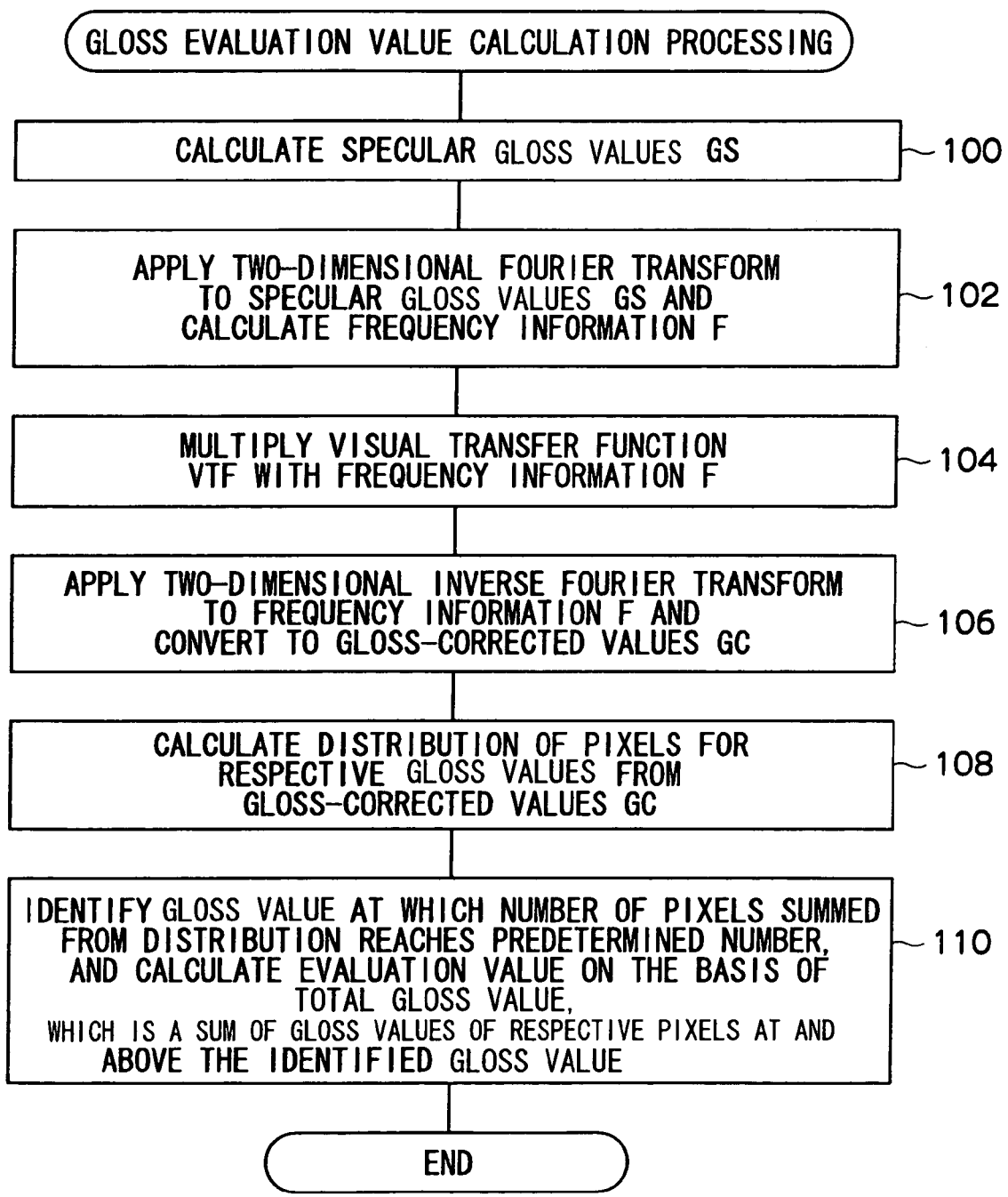
FIG. 4 is a flowchart showing a flow of gloss evaluation value calculation processing relating to the first embodiment of the present invention.

Next, operations of the gloss measurement apparatus 10 when the aforementioned gloss evaluation value calculation processing is executed will be described with reference to FIG. 4. FIG. 4 is a flowchart showing a flow of the gloss evaluation value calculation processing.

In step 100 of FIG. 4, the image data stored at the image storage section 30 is read and, from the light amounts R(x,y), G(x,y) and B(x,y) for each of R, G and B of the respective pixels of the image represented by the image data, specular gloss values GS(x,y) of the respective pixels are calculated using the aforementioned equation (1).

Next, in step 102, a two-dimensional Fourier transform is performed on the specular gloss values GS(x,y) calculated in step 100, to calculate the frequency information F(u,v) representing specular gloss values in the spatial frequency domain.

Next, in step 104, the frequency information F(u,v) calculated in step 102 is converted to frequency information in polar co-ordinates F(f,θ), and the frequency information F(f, θ) is multiplied by the visual transfer function VTF(f) illustrated in the aforementioned equation (2) to perform the correction for matching human visual characteristics.

Next, in step 106, a two-dimensional inverse Fourier transform is performed on the frequency information F(u,v) which has been corrected in step 104, to convert the same to the gloss-corrected values GC(x,y), which have been corrected, in the image space domain.

Figure 9:
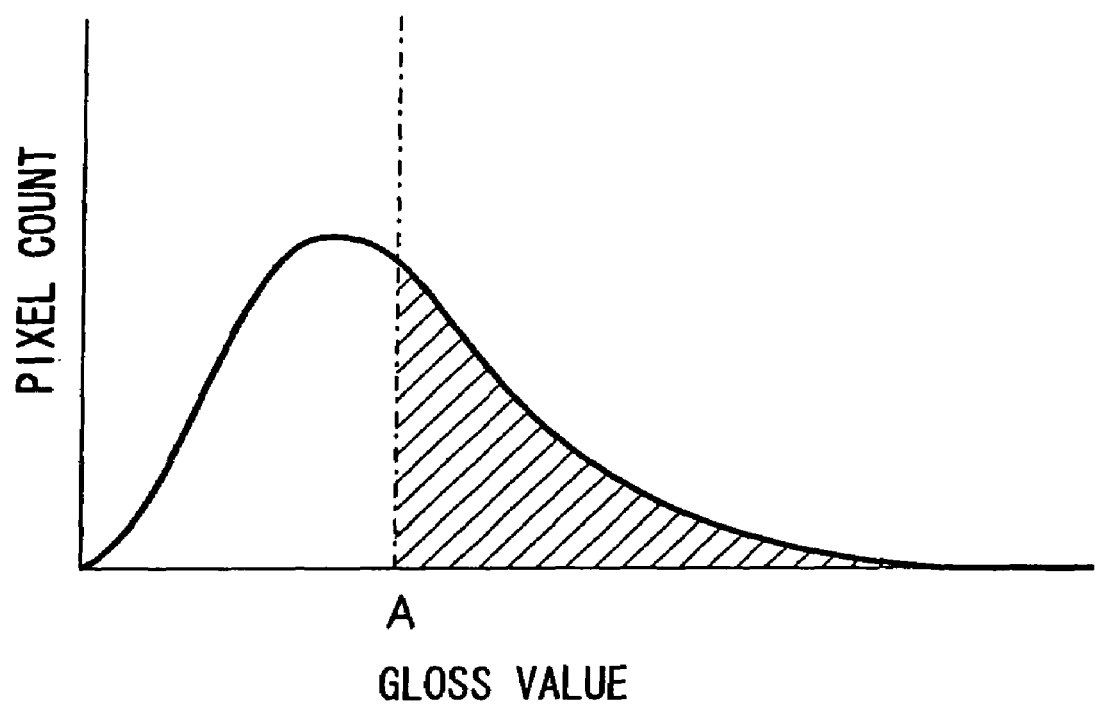
FIG. 9 is a graph showing a distribution of pixel counts for respective gloss values of gloss-corrected values GC in relation to the first embodiment of the present invention.

Next, in step 108, the distribution of pixel counts for respective gloss values of an image represented by the converted gloss-corrected values GC(x,y) is calculated (see FIG. 9).

Next, in step 110, pixel counts in the calculated distribution of pixel counts of respective gloss values are summed from the side of high gloss value, and the gloss value A at which the aforementioned predetermined number is reached is identified. The total gloss value GM, which is the sum of gloss values of pixels from the gloss value A upward (the shaded area in FIG. 9), is found. A logarithm of the total gloss value GM is outputted to the display section 19 to serve as the gloss evaluation value VG. Thereafter, this gloss evaluation value calculation processing ends.

Figure 5B:
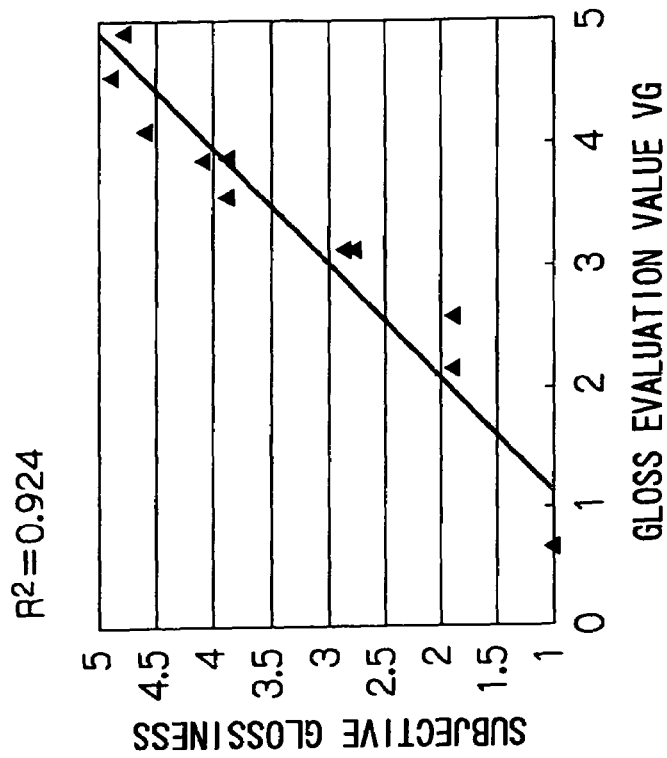
FIG. 5B is a graph showing results when gloss values of the predetermined objects to be measured are measured by a gloss measurement method of the first embodiment of the present invention.
Figure 5A:
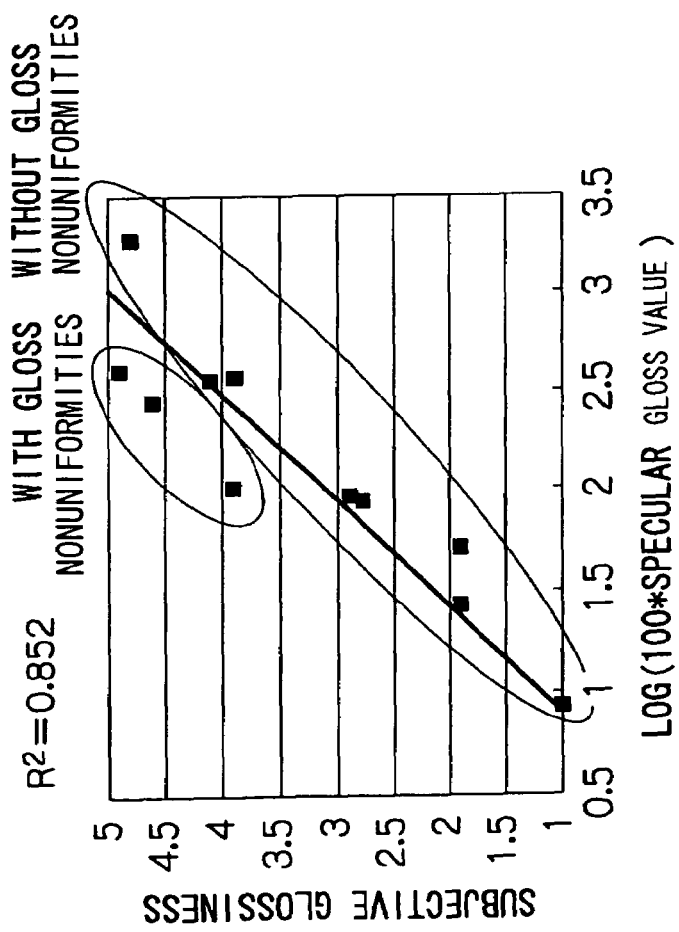
FIG. 5A is a graph showing results when gloss values of predetermined objects to be measured are measured by a specular gloss measurement method (JIS-Z8741)

FIGS. 5A and 5B show examples of measurement results of gloss value of matching objects to be measured 12 (hereinbelow referred to as object to be measured) by each of the gloss measurement apparatus 10 relating to the present embodiment and a specular gloss measurement method (JIS-Z8741). For FIG. 5A, specular gloss values are measured by the specular gloss measurement method with an incidence angle on the object to be measured θ=20°, the measured specular gloss values are multiplied by 100 and log-transformed, and these values are shown on the horizontal axis. In FIG. 5B, calculation results for the objects to be measured of gloss evaluation values VG according to the gloss measurement apparatus 10 relating to the present embodiment are shown on the horizontal axis. Meanwhile, the vertical axes of FIGS. 5A and 5B are subjective glossinesses obtained by performing sensory evaluation tests with human vision on the same predetermined objects to be measured, and show larger numerical values for higher subjective glossinesses.

Here, for the present embodiment, the plural objects to be measured which are targets of measurement are prepared and measurements are performed thereon. Images of a primary color (black alone) and of a tertiary color (a black obtained by combining all three of cyan (C), magenta (M) and yellow (Y), known as a 'process black') are respectively formed by an image-forming device with an electrophotographic system or an inkjet system. Specular gloss values of the respective objects to be measured at the incidence angle θ=20° according to the specular gloss measurement method are within the range 0.2 to 29.0.

As shown in FIG. 5A, a contribution ratio ($R^2$) between the values of specular gloss value with the incidence angle θ=20°, which have been multiplied by 100 and log-transformed, and the subjective glossinesses is 0.852.

Now, as a result of assiduous investigations by the present inventor, it has been found that a factor which reduces a contribution ratio between specular gloss values measured by the specular gloss measurement method and subjective glossinesses is nonuniformities in gloss of the objects to be measured 12.

Thus, as shown in FIG. 5A, when there are inconsistencies in gloss, there is a tendency for a specular gloss value to be lower even for subjective glossinesses which are the same, or for a subjective glossiness to be higher even for specular gloss values which are the same. This factor is thought to be because humans judge glossiness by observing areas of high gloss rather than average gloss of an object to be measured.

Accordingly, in the gloss measurement apparatus 10 relating to the first embodiment, in the distribution of pixel counts of respective gloss values of the gloss-corrected values GC(x, y), the pixel counts are summed from the side of high gloss value, and the gloss value A at which this pixel count is half of the total number of pixels is identified. A total gloss value GM, which is a sum of gloss values of each pixel from the gloss value A upward, is log-transformed, and this value serves as the gloss evaluation value VG.

FIG. 5B shows measurement results from the gloss measurement apparatus 10 relating to the present embodiment. A contribution ratio ($R^2$) between the gloss evaluation values VG and the subjective glossinesses is very high, being 0.924. Therefore, it is possible, by using the total gloss value GM to calculate the gloss evaluation value VG, to obtain a measurement result which attains correspondence with a subjective glossiness even if there are gloss nonuniformities at the object to be measured 12.

Thus, according to the gloss measurement apparatus 10 relating to the first embodiment, even when there are gloss nonuniformities at the object to be measured 12, because the gloss evaluation value VG is found on the basis of the distribution of pixel counts of respective gloss values of the gloss-corrected values GC(x,y), it is possible to find gloss evaluation values VG which attain correspondence with subjective glossinesses more reliably than by previous methods.

According to the first embodiment as described above, an acquisition component (here, the CCD area sensor 22A) acquires image information in accordance with received light amounts, for each of predetermined pixels, of specular reflected light from a surface of an object to be measured, a pixel gloss value calculation component (here, the specular gloss value calculation section 32) calculates gloss values of the respective pixels on the basis of the received light amounts at the respective pixels of the image information acquired by the acquisition component, and an evaluation value calculation component (here, the evaluation value calculation section 38) calculates an evaluation value representing a glossiness of the object to be measured on the basis of the gloss values calculated by the pixel gloss value calculation component. Thus, an evaluation value which attains correspondence with a subjective glossiness even if there are nonuniformities in gloss at an object to be measured can be calculated.

Further, according to the first embodiment, the evaluation value calculation component is provided with a distribution calculation component (here, the distribution calculation section 36) which calculates a distribution of pixel counts for respective gloss values from the gloss values of the respective pixels, and the evaluation value calculation component identifies a gloss value at which a number of pixels, which is summed from a side of high gloss value in the distribution calculated by the distribution calculation component, reaches a predetermined number, and calculates the evaluation value representing glossiness of the object to be measured on the basis of a total gloss value, which is a sum of gloss values of the respective pixels at and above the identified gloss value. Thus, because the evaluation value is calculated on the basis of the total gloss value, which is a sum of gloss values of pixels of a high-gloss value region, it is possible to obtain a measurement result which attains correspondence of the calculated evaluation value with a subjective glossiness even if there are inconsistencies in gloss at the object to be measured.

Further still, according to the first embodiment, a correction component (here, the correction section 34) is further provided, which performs a correction to cause a spatial frequency characteristic of the gloss values of the respective pixels calculated by the pixel gloss value calculation component to correspond with a spatial frequency characteristic of human vision. The evaluation value calculation component calculates the evaluation value representing the glossiness of the object to be measured on the basis of the gloss values of respective pixels which have been corrected by the correction component. Thus, the calculated evaluation value and the subjective glossiness can attain greater correspondence.

Further again, according to the first embodiment, the correction component is structured to include a two-dimensional Fourier transform component (here, the two-dimensional Fourier transform section 40), a multiplication component (here, the visual characteristic correction section 42) and a two-dimensional inverse Fourier transform component (here, the two-dimensional inverse Fourier transform section 44). The two-dimensional Fourier transform component performs a two-dimensional Fourier transform on the gloss values of respective pixels calculated by the pixel gloss calculation component, thus converting the gloss values to gloss values in the spatial frequency domain. The multiplication component multiplies a predetermined visual transfer function, which corresponds to spatial frequency characteristics of human vision, with the frequency information representing the gloss values of respective pixels that have been transformed to spatial frequency domain information by the two-dimensional Fourier transform component. The two-dimensional inverse Fourier transform component performs a two-dimensional inverse Fourier transformation on the results of multiplication by the multiplication component, thus transforming the same to gloss values of respective pixels which are pixels in the image space domain. Thus, it is possible to cause the acquired image to correspond with a spatial frequency characteristic of human vision.

Anyway, for the first embodiment, a case of calculating specular gloss values GS(x,y) at respective pixels of an image by equation (1) from light amounts R(x,y), G(x,y) and B(x,y) of each of R, G and B of the respective pixels of the image has been described. However, the present invention is not limited thus. For example, because a correlation between specular gloss values GS(x,y) and light amounts G(x,y) is high, it is possible to calculate the specular gloss values using just the light amounts G(x,y). In such a case, similar effects to the present embodiment can be achieved.

Moreover, for the first embodiment, a case has been described in which the pixel counts are summed from the side of high gloss value to a gloss value A at which this number of pixels reaches half of a total number of pixels, and gloss values of respective pixels at and above the gloss value A are summed. However, the present invention is not limited thus. A range of pixel counts to be summed may be suitably altered to, for example, a number of pixels which is a predetermined proportion (for example, 30%) of a total number of pixels from the side of high gloss value or a predetermined number of pixels (for example, 100 pixels) from the side of high gloss value, or the like. In such cases, similar effects to the present embodiment can be achieved.

Second Embodiment

For a second embodiment, an example will be described in which an index value representing glossiness is calculated from the gloss-corrected values GC, and an evaluation value which attains correspondence with a subjective glossiness is calculated by an operation from the calculated index value representing gloss value. Herein, structure of the gloss measurement apparatus 10 in relation to the second embodiment is the same as in FIG. 1, so descriptions thereof will be omitted here.

Figure 6:
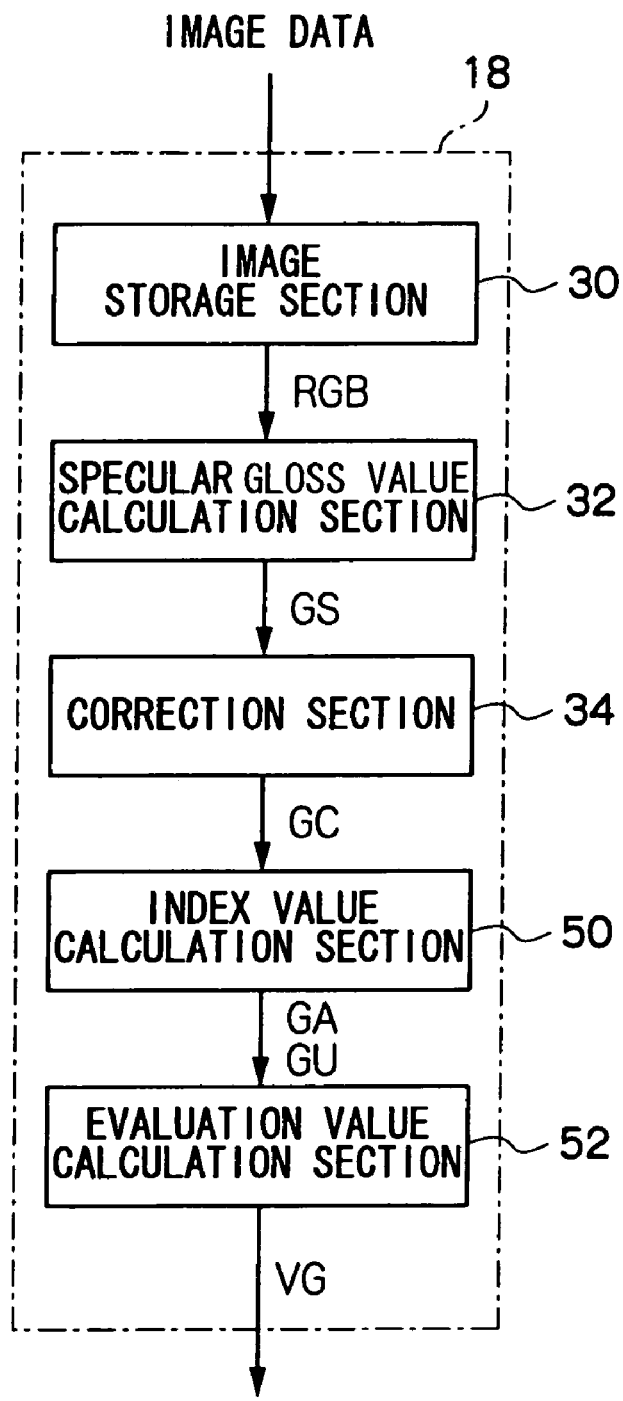
FIG. 6 is a functional block diagram showing detailed structure of an image processing section relating to a second embodiment of the present invention.

FIG. 6 shows detailed structure of the image processing section 18 in relation to the second embodiment. Here, structural elements that are the same in FIG. 6 as in FIG. 2 are assigned the same reference numerals, and descriptions thereof will not be given.

The image processing section 18 relating to the second embodiment is provided with an index value calculation section 50 and an evaluation value calculation section 52. On the basis of the gloss-corrected values GC of respective pixels which are outputted from the correction section 34, the index value calculation section 50 calculates an average gloss index value GA, which represents an average value of gloss value at all the pixels, and a gloss nonuniformity index value GU, which represents a degree of occurrence of nonuniformities in gloss. On the basis of the average gloss index value GA and the gloss nonuniformity index value GU which have been calculated by the index value calculation section 50, the evaluation value calculation section 52 calculates an evaluation value which attains correspondence with a subjective glossiness.

Here, the index value calculation section 50 relating to the present embodiment calculates a logarithm (log(GC_ave)) of an average value GC_ave of all the pixels of the gloss-corrected values GC(x,y), to serve as the average gloss index value GA. The index value calculation section 50 also finds a standard deviation GC_std of the gloss-corrected values GC(x,y), and divides a logarithm of the standard deviation GC_std by the above-mentioned logarithm of the average value of all pixels GC_ave to calculate a value (log(GC_std)/log(GC_ave)) which serve as the gloss nonuniformity index value GU. Note that this average value of all pixels GC_ave is an index which corresponds to a logarithm of a specular gloss value that is measured by the specular gloss measurement method (JIS-Z8741) with incidence angle $\theta=20°$.

Further, the evaluation value calculation section 52 relating to the present embodiment, from the average gloss index value GA and gloss nonuniformity index value GU which have been calculated by the index value calculation section 50, performs a weighting operation such that the gloss evaluation value VG is larger when the average gloss index value GA is larger and such that the gloss evaluation value VG is larger when the gloss nonuniformity index value GU is larger, and the evaluation value calculation section 52 calculates an evaluation value representing glossiness of the object to be measured by finding a linear sum of the values obtained by this weighting.

That is, by using a weighted linear sum as in, for example, the following equation (3), the evaluation value calculation section 52 calculates a gloss evaluation value VG which can ameliorate the effects of gloss nonuniformities.

$$VG = p1 \times GA + p2 \times GU + p3 \quad (3)$$

Because, as described above, the average gloss index value GA (log(GC_ave)) is the logarithm of the average value of all pixels GC_ave and the gloss nonuniformity index value GU (log(GC_std)/log(GC_ave)) is the value in which the logarithm of the standard deviation GC_std is divided by the logarithm of the average value of all pixels GC_ave, a conversion as shown in the following equation (4) is possible.

$$VG = p1 \times (\log(GC\_ave)) + p2 \times (\log(GC\_std)/\log(GC\_ave)) + p3 \quad (4)$$

Here, for the coefficients p1 to p3 in equations (3) and (4), a predetermined measurement subject 12 is captured by the present gloss measurement apparatus 10, and an average value of all pixels GC_ave and a standard deviation GC_std are found from the obtained gloss-corrected values GC(x,y) of the predetermined measurement subject 12. Optimum values of the coefficients p1 to p3 are found in advance by regression analysis of equations (3) and (4), using this average value GC_ave and standard deviation GC_std and a subjective glossiness obtained from a sensory evaluation test with human vision of the same predetermined measurement subject 12, and these optimum values are employed. Note that the coefficient p3 is a correction value for preventing the gloss evaluation value VG found by equations (3) and (4) having a negative value.

Figure 7:
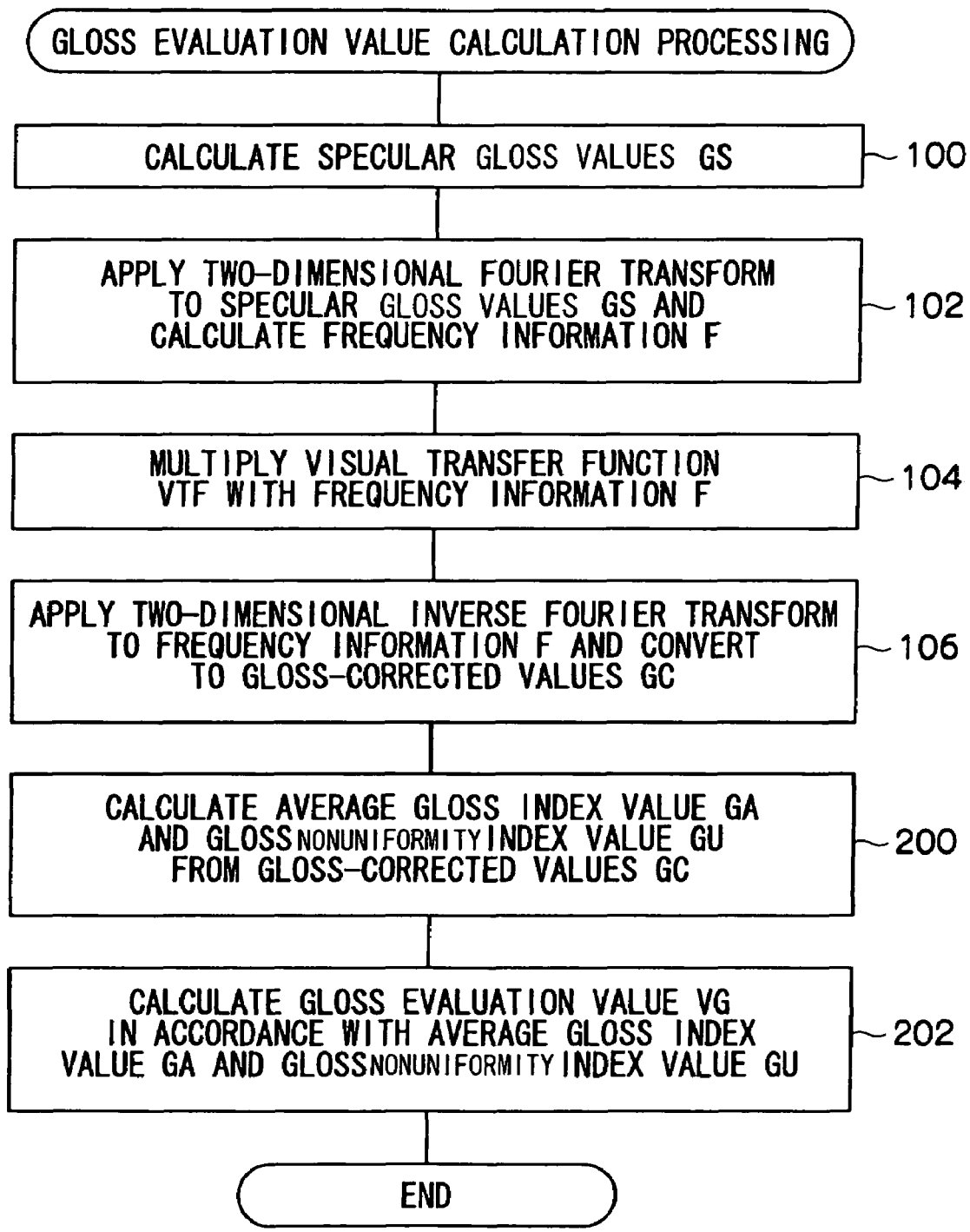
FIG. 7 is a flowchart showing a flow of gloss evaluation value calculation processing in the second embodiment of the present invention.

FIG. 7 shows gloss evaluation value calculation processing relating to the second embodiment. Here, processes in FIG. 7 that are the same as in FIG. 4 are assigned the same reference numerals as in FIG. 4, descriptions thereof are omitted, and only variant portions will be described.

In step 200 of FIG. 7, the average value GC_ave of all pixels of the gloss-corrected values GC(x,y), which have been converted in step 106, is log-converted to calculate the average gloss index value GA. Further, the standard deviation GC_std of the gloss-corrected values GC(x,y) is found, and a logarithm of this standard deviation GC_std is divided by the logarithm of the average value of all pixels GC_ave to calculate the gloss nonuniformity index value GU.

Then, in step 202, the calculation of the above-mentioned equation (3) is performed using the average gloss index value GA and gloss nonuniformity index value GU which have been calculated in step 200, the gloss evaluation value VG is calculated and outputted to the display section 19, and then this gloss evaluation value calculation processing ends.

Figure 8:
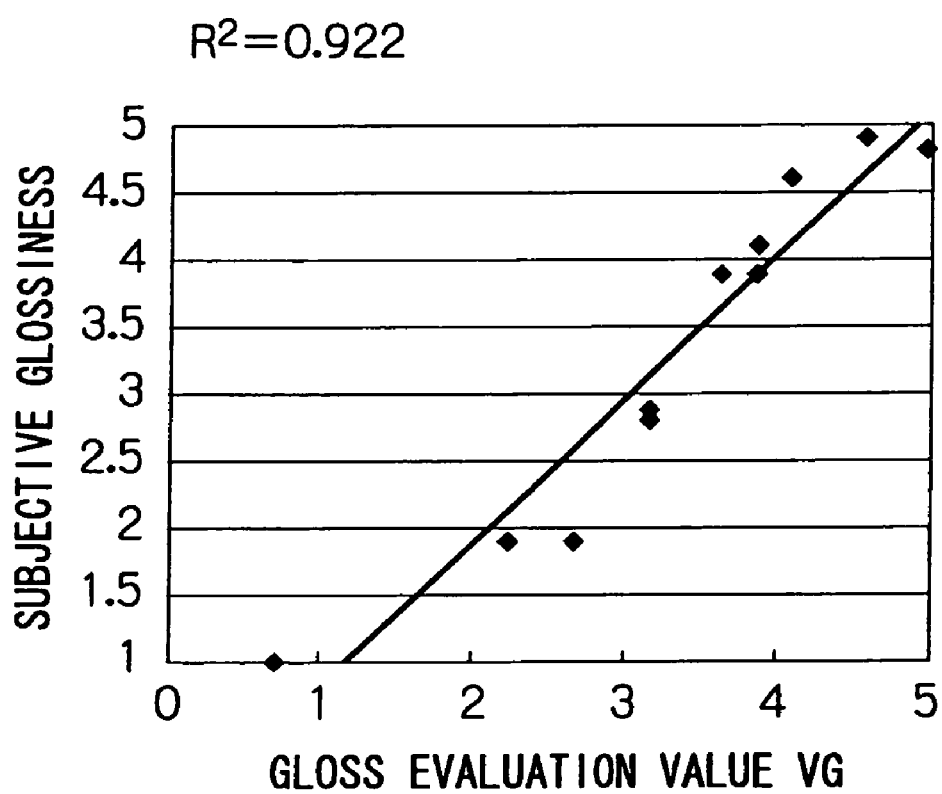
FIG. 8 is a graph showing results when gloss values of the predetermined objects to be measured are measured by a gloss measurement method relating to the second embodiment of the present invention.

FIG. 8 shows an example of results of calculations of gloss evaluation values VG of predetermined objects to be measured 12 by the gloss measurement apparatus 10 relating to the second embodiment. For FIG. 8, results are calculated of gloss evaluation values VG for objects to be measured 12 (below referred to as objects to be measured) the same as the aforementioned objects to be measured 12 measured by the specular gloss measurement method (see FIG. 5A). Subjective glossinesses, which are shown by the vertical axis of FIG. 8, are the subjective glossinesses according to human vision that have been obtained by performing sensory evaluation tests on the objects to be measured.

As mentioned earlier, the specular gloss values of the objects to be measured shown in FIG. 5A, which are measured by the specular gloss measurement method, have a tendency when there are gloss nonuniformities, as described earlier, for a specular gloss value to be lower even for subjective glossinesses which are the same, or a tendency for a subjective glossiness to be higher even for specular gloss values which are the same. According to the diligent investigations of the present inventor, this factor is thought to be because humans judge glossiness not just by average gloss of an object to be measured but by observing presence/absence and frequencies of gloss nonuniformities.

Accordingly, in the gloss measurement apparatus 10 relating to the second embodiment, the gloss evaluation value VG is found from a weighted linear sum of the average gloss index value GA and the gloss nonuniformity index value GU.

FIG. 8 is a graph showing a correlation of gloss evaluation values VG found using equation (3) with subjective glossinesses. Here, the weighting coefficients, from regression analysis of the subjective glossinesses found from sensory evaluation tests, are, respectively, p1=1.259, p2=3.949 and p3=−3.643.

The contribution ratio ($R^2$) indicating a correlation between the subjective glossinesses and the logarithms of specular gloss values with incidence angle $\theta=20°$ shown in FIG. 5A is 0.852. In contrast, the contribution ratio ($R^2$) indicating a correlation between the subjective glossinesses and the gloss evaluation values VG measured by the gloss measurement apparatus 10 relating to the second embodiment, shown in FIG. 8, is extremely high, being 0.922. Therefore, because the gloss evaluation value VG is found, by multiplying the respective predetermined weightings with the average gloss index value GA and gloss nonuniformity index value GU calculated from the gloss-corrected values GC(x,y), such that the gloss evaluation value VG is larger when the average gloss index value GA is larger and such that the gloss evaluation value VG is larger when the gloss nonuniformity index value GU is larger, even if there are nonuniformities in gloss at the object to be measured 12, a result attaining correspondence with a subjective glossiness can be obtained.

Thus, according to the gloss measurement apparatus 10 relating to the second embodiment, even when there are gloss nonuniformities at the object to be measured 12, it is possible to find a gloss evaluation value VG which attains correspondence with a subjective glossiness more reliably than by previous methods, with an extremely simple method in which the gloss evaluation value VG is found by a weighted linear sum of the average gloss index value GA and the gloss nonuniformity index value GU.

According to the second embodiment as described above, the evaluation value calculation component is provided with an index value calculation component (here, the index value calculation section 50) which, on the basis of the gloss values of the respective pixels, calculates an average gloss index value representing an average value of gloss values of all the pixels and a gloss nonuniformity index value representing a degree of occurrence of nonuniformities in gloss. The average gloss index value and gloss nonuniformity index value are respectively multiplied with predetermined weighting coefficients, and the evaluation value representing glossiness of the object to be measured is calculated by finding a linear sum of the obtained values, such that the evaluation value representing glossiness of the object to be measured increases when the average gloss index value increases and the evaluation value representing glossiness of the object to be measured increases when the gloss nonuniformity index value increases. Thus, it is possible to obtain a measurement result which attains correspondence with the subjective glossiness even if there are irregularities in gloss at the object to be measured 12.

Further, according to the second embodiment, the gloss nonuniformity index value is a value in which a standard deviation value of gloss values of the respective pixels is divided by the average gloss index value. Thus, a gloss nonuniformity index value can be found that is suitable in accordance with the gloss nonuniformities that occur.

Anyway, for the first and second embodiments, a case in which the specular gloss value calculation section 32 calculates the specular gloss values GS(x,y) from the light amounts R(x,y), G(x,y) and B(x,y) of each of R, G and B of the respective pixels of the image has been described. However, the present invention is not limited thus. For example, calculations of specular gloss values GS(x,y) are also possible with tristimulus values X, Y, Z or CIELAB color values L*, a*, b* of the respective pixels of the image, or the specular gloss values GS(x,y) could be calculated using visual reflectances Y and brightnesses L*. In such cases, similar effects to the present embodiment can be achieved.

Further, at the gloss measurement apparatus 10 relating to the first or second embodiment, the respective functions illustrated for the specular gloss value calculation section 32, the correction section 34, the distribution calculation section 36, the evaluation value calculation section 38, the index value calculation section 50 and the evaluation value calculation section 52 may be implemented by software.

Third Embodiment

For a third embodiment, an example will be described in which, of light that is emitted from the light source, specular reflected light which is regularly reflected by the object to be measured and diffuse reflected light which is diffusely reflected by the object to be measured are respectively captured, and an evaluation value representing glossiness of the object to be measured is calculated on the basis of the image information obtained by this imaging.

Figure 10:
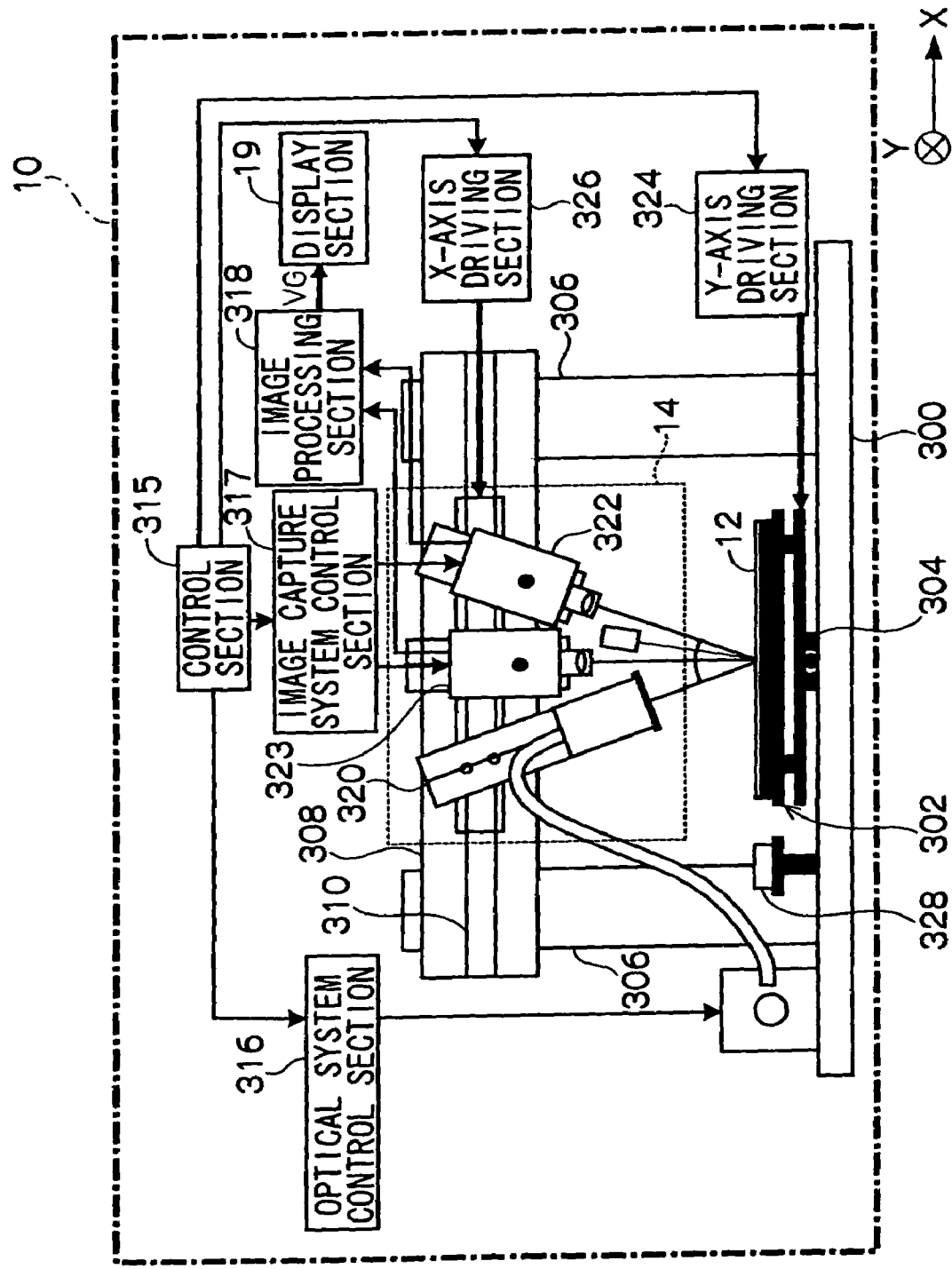
FIG. 10 is a diagram showing schematic structure of a gloss measurement apparatus relating to a third embodiment of the present invention.

FIG. 10 shows general structure of the gloss measurement apparatus 10 in relation to the third embodiment. Here, structural elements that are the same in FIG. 10 as in the gloss measurement apparatus 10 relating to the first embodiment (FIG. 1) are assigned the same reference numerals, and will not be described here.

As shown in FIG. 10, the gloss measurement apparatus 10 is equipped with a stage 302 on a platform 300. The stage 302 adheres the object to be measured 12 to a surface thereof with electrostatic force, to retain the object to be measured 12. Sliding rails 304 are provided at an upper face of the platform 300, along a direction perpendicular to the paper surface of FIG. 10 (referred to as the Y direction hereafter). The platform 300 supports the stage 302 via the sliding rails 304. Thus, the stage 302 is made to be movable in the Y direction along the sliding rails 304.

A pair of pillars 306 are respectively provided standing from the platform 300, at outer sides of two width direction end portions of the stage 302. A support member 308 spans between this pair of pillars 306. A guide rail 310 is provided at a side face of the support member 308, along an X direction which is parallel to the stage surface and intersects the Y direction (i.e., the left-right direction of the paper surface of FIG. 10). The support member 308 supports the optics section 14 via the guide rail 310. Thus, the optics section 14 is made to be movable along the guide rail 310 in the X direction.

The optics section 14 is provided with a light source 320, a specular reflected light capture section 322 and a diffuse reflected light capture section 323. The light source 320 emits light onto the object to be measured 12, the specular reflected light capture section 322 captures specular reflected light which has been regularly reflected by the object to be measured 12, and the diffuse reflected light capture section 323 captures diffuse reflected light which has been diffusely reflected by the object to be measured 12.

The gloss measurement apparatus 10 is further equipped with an optical system control section 316, an image capture system control section 317, an image processing section 318, a Y-axis driving section 324, an X-axis driving section 326 and a control section 315. The optical system control section 316 controls operations of the light source 320. The image capture system control section 317 controls capture operations of the specular reflected light capture section 322 and the diffuse reflected light capture section 323. The image processing section 318 calculates an evaluation value relating to glossiness of the object to be measured 12 on the basis of image data acquired by image capture by the specular reflected light capture section 322 and diffuse reflected light capture section 323 in accordance with control by the image capture system control section 317. The Y-axis driving section 324 moves the stage 302 along the sliding rails 304 in the Y direction by driving force of a motor. The X-axis driving section 326 moves the optics section 14 along the guide rail 310 in the X direction by driving force of a motor. The control section 315 controls operations of the optical system control section 316, the image capture system control section 317, the Y-axis driving section 324 and the X-axis driving section 326, and controls gloss measurement processing.

In accordance with controls from the control section 315, the stage 302 is moved in the Y direction by the Y-axis driving section 324, and the optics section 14 is moved in the X direction by the X-axis driving section 326. Thus, the gloss measurement apparatus 10 can cause the imaging section to oppose an arbitrary position of the object to be measured 12 that has been placed on the stage 302. Because the stage 302 and the optics section 14 are made to be movable thus, a lateral range of the object to be measured 12 placed on the stage 302 serves as a measurement range, and measurements at high speed in a compact space are possible.

Further, a standard surface 328 (a black glass surface whose refractive index is 1.567) is provided at the gloss measurement apparatus 10, adjacent to the stage 302 on the platform 300. It is possible to move the stage 302 in the Y direction with the Y-axis driving section 324 and move the optics section 14 in the X direction with the X-axis driving section 326 to cause the optics section 14 to oppose the standard surface 328.

Next, structure of the optics section 14 relating to the present embodiment will be described in detail with reference to FIG. 11.

Figure 11:
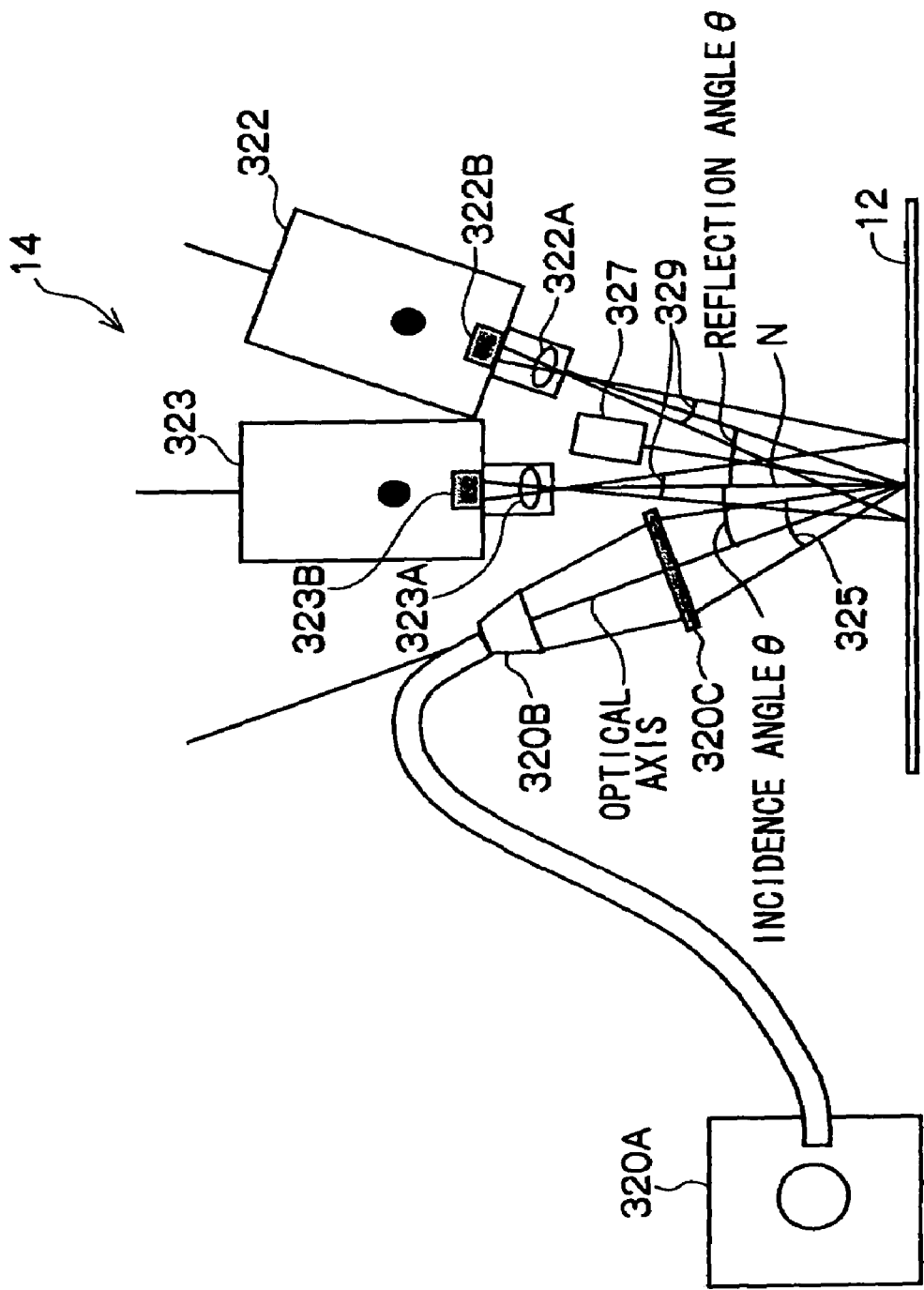
FIG. 11 is a diagram showing detailed structure of an optics section relating to the third embodiment of the present invention.

As is shown in FIG. 11, the light source 320 is disposed at a position from which an optical axis of the light emitted at the object to be measured 12 is incident at a pre-specified incidence angle θ (in the present embodiment, the incidence angle θ=20°) with respect to a normal line N of the object to be measured 12. The specular reflected light capture section 322 is disposed on the optical axis of regularly reflected light which has been incident on the object to be measured 12 at the incident angle θ (i.e., a reflection direction with a reflection angle θ=20° relative to the normal line N). The diffuse reflected light capture section 323 is disposed at a direction (in the present embodiment, the direction of the normal line N) which differs from the specular reflection direction of the light that is incident at the incidence angle θ.

The light source 320 is provided with a halogen fiber light source 320A, a condensing lens 320B and a diffuser 320C. The halogen fiber light source 320A emits light, the condensing lens 320B condenses the emitted light in a predetermined direction, and the diffuser 320C diffuses the light that has been condensed by the condensing lens 320B. The light source 320 is an emitting optical system which emits light having a predetermined incidence angle deviation 325 (in the present embodiment, ±3.1°) about the optical axis of the light that is emitted onto the object to be measured 12. This incidence angle deviation 325 is an angle, with respect to the optical axis of the light that is incident on the object to be measured 12 from the light source 320, at which light that has been diffused by the diffuser 320C is incident. In the present embodiment, the incidence angle deviation 325 is set to a value close to observation conditions in ordinary offices by alteration of a distance between the diffuser 320C and the object to be measured 12.

The specular reflected light capture section 322 is provided with a focusing lens 322A and a CCD area sensor 322B. The focusing lens 322A focuses incident light to a predetermined position. A light-receiving surface of the CCD area sensor 322B is disposed at this focusing position, generates image data of each of the colors R, G and B, which represents an image of the focused specular reflected light, and outputs the image data to the image processing section 18. The specular reflected light capture section 322 acts as a focusing optical system with an angle of view 329 of 3.9°. This angle of view 329 is set by the combination of the CCD area sensor 322B and the focusing lens 322A. In the present embodiment, the angle of view 329 is set to a value close to a viewing angle of a case of viewing of the object to be measured by a human. In this manner, a correspondence between gloss values measured by the gloss measurement apparatus 10 and subjective glossinesses is attained by bringing the optical system close to observation conditions in ordinary offices.

The diffuse reflected light capture section 323 is provided with a CCD area sensor 323B and a focusing lens 323A, with a structure similar to the specular reflected light capture section 322. Herein, the CCD area sensors 322B and 323B relating to the present embodiment have pixel counts of 1392× 1040 pixels, resolutions of 13.6 μm and measurement regions of 20×15 mm.

The optics section 14 is also provided with a laser pointer 327, which outputs laser light. The laser pointer 327 is disposed such that the outputted laser light is positioned at the middle of an image capture target range according to the specular reflected light capture section 322 and the diffuse reflected light capture section 323.

Next, structure of the image processing section 318 relating to the present embodiment will be described in detail with reference to FIG. 12.

Figure 12:
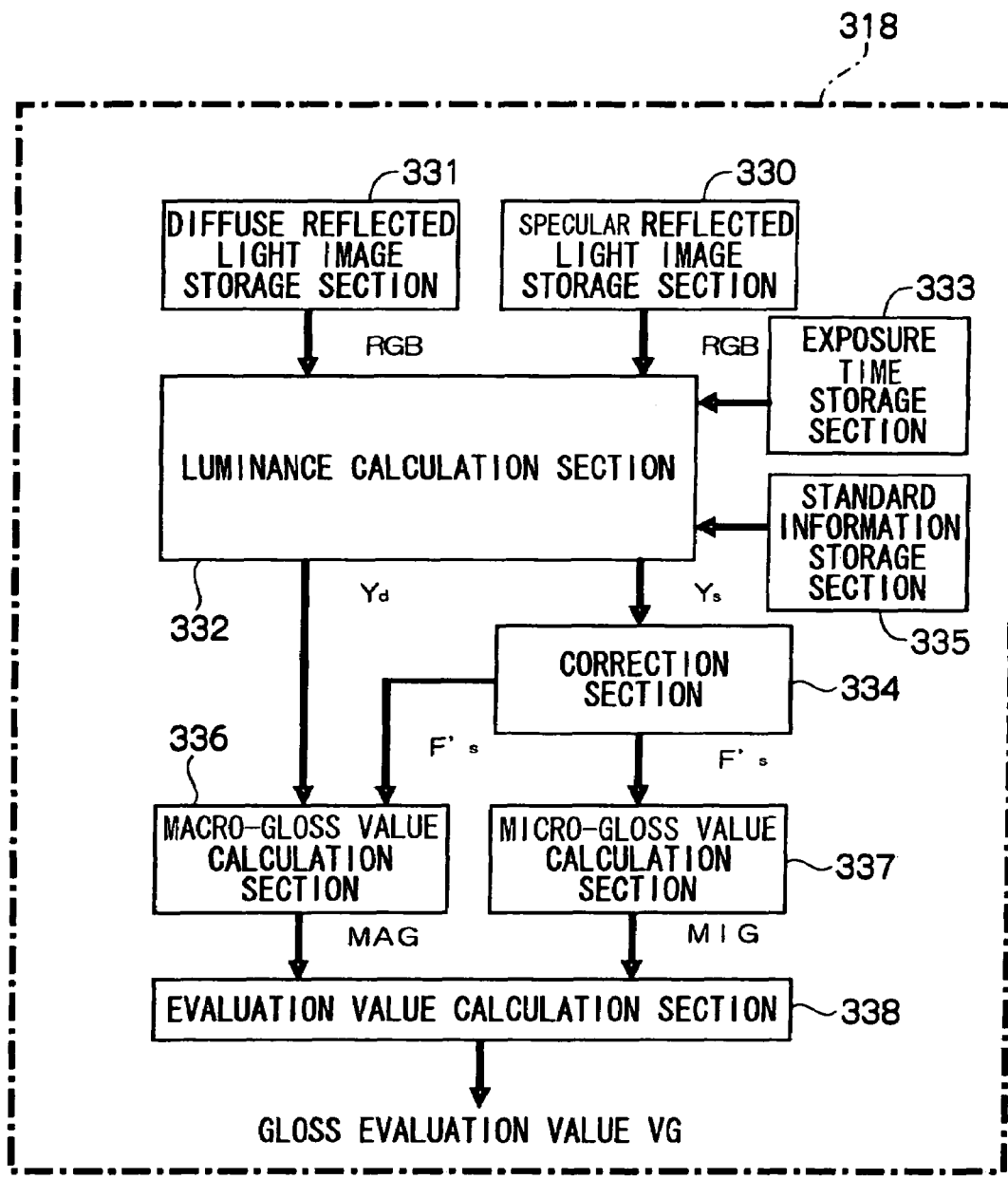
FIG. 12 is a functional block diagram showing detailed structure of an image processing section relating to the third embodiment of the present invention.

As shown in FIG. 12, the image processing section 318 is provided with a specular reflected light image storage section 330, a diffuse reflected light image storage section 331, an exposure time storage section 333 and a standard information storage section 335. The specular reflected light image storage section 330 stores specular reflected light image data obtained by capture by the specular reflected light capture section 322. The diffuse reflected light image storage section 331 stores diffuse reflected light image data obtained by capture by the diffuse reflected light capture section 323. The exposure time storage section 333 stores an exposure time $ET_s$ of the specular reflected image data at the specular reflected light capture section 322 and an exposure time $ET_d$ of the diffuse reflected light image data at the diffuse reflected light capture section 323. The standard information storage section 335 stores average values of R, G and B and an exposure time $ET_o$ of the specular reflected light image data of the standard surface 328. Here, the specular reflected light image storage section 330, diffuse reflected light image storage section 331, exposure time storage section 333 and standard information storage section 335 relating to the present embodiment are structured by a hard disk, but this is not a limitation and the same could be structured by other non-volatile memory such as flash memory or the like.

The image processing section 318 is also equipped with a luminance calculation section 332, a correction section 334, a macro-gloss value calculation section 336, a micro-gloss value calculation section 337 and an evaluation value calculation section 338. The luminance calculation section 332 calculates specular reflected light-luminance image data $Y_s$ of respective pixels on the basis of the specular reflected light image data, and calculates diffuse reflected light-luminance image data $Y_d$ of respective pixels on the basis of the diffuse reflected light image data. The correction section 334 calculates a corrected frequency spectrum $F'_s$ in which a spatial frequency characteristic of the specular reflected light-luminance image data $Y_s$ calculated by the luminance calculation section 332 has been corrected. The macro-gloss value calculation section 336 calculates a macro-gloss value MAG from the correction frequency spectrum $F'_s$ that has been corrected by the correction section 334 and the diffuse reflected light-luminance image data calculated by the luminance calculation section 332. The micro-gloss value calculation section 337 calculates a micro-gloss value MEG from the corrected frequency spectrum $F'_s$. The evaluation value calculation section 338 calculates a gloss evaluation value VG from the macro-gloss value MAG and the micro-gloss value MIG.

Now, if light amounts for each of R, G and B of pixels (x,y) of the image represented by the specular reflected light image data that is stored at the specular reflected light image storage section 330 are ($R_s(x,y)$, $G_s(x,y)$, $B_s(x,y)$) and light amounts for each of R, G and B of the pixels (x,y) of the image represented by the diffuse reflected light image data that is stored at the diffuse reflected light image storage section 331 are ($R_d(x,y)$, $G_d(x,y)$, $B_d(x,y)$), the luminance calculation section 332 relating to the present embodiment calculates the specular reflected light-luminance image data $Y_s(x,y)$ and the diffuse reflected light-luminance image data $Y_d(x,y)$, which are normalized by the specular reflected light image data of the standard surface 328, by the following equations (5) and (6).

$$Y_s(x,y) = \frac{\left[\frac{K_r \cdot R_s(x,y) + K_g \cdot G_s(x,y) + K_b \cdot B_s(x,y)}{ETs}\right]}{\left[\frac{K_r \cdot R_o + K_g \cdot G_o + K_b \cdot B_o}{ETo}\right]} \quad (5)$$

$$Y_d(x,y) = \frac{\left[\frac{K_r \cdot R_d(x,y) + K_g \cdot G_d(x,y) + K_b \cdot B_d(x,y)}{ETd}\right]}{\left[\frac{K_r \cdot R_o + K_g \cdot G_o + K_b \cdot B_o}{ETo}\right]} \quad (6)$$

Wherein:

$ET_s$ is the exposure time of specular reflected light imaging of the object to be measured 12;

$ET_d$ is the exposure time of diffuse reflected light imaging of the object to be measured 12;

$R_o$, $G_o$ and $B_o$ are the average values of R, G and B of the specular reflected light image data of the standard surface 328;

$ET_o$ is the exposure time of specular reflected light imaging of the standard surface 328; and $K_r$, $K_g$ and $K_b$ are conversion coefficients.

Here, for the conversion coefficients $K_r$, $K_g$ and $K_b$ in equations (5) and (6), diffuse reflected light of plural color patches printed from a printer using an electrophotography system are respectively measured by both the gloss measurement apparatus 10 and a previously known spectral radiance measurement instrument. Optimum values of the conversion coefficients $K_r$, $K_g$ and $K_b$ are found by multiple regression analysis of luminances calculated from R, G and B values measured by the gloss measurement apparatus 10 and luminances measured by the spectral radiance measurement instrument, and these optimum values are employed. In the present embodiment, the applied values are $K_r$=0.120, $K_g$=0.266 and $K_b$=−0.047.

Next, structure of the correction section 334 relating to the present embodiment will be described in detail with reference to FIG. 13.

Figure 13:
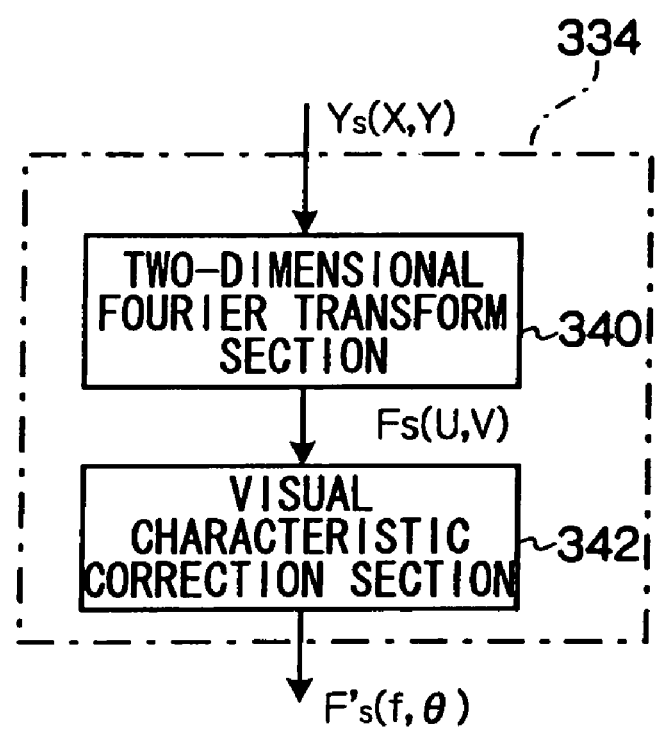
FIG. 13 is a functional block diagram showing detailed structure of a correction section relating to the third embodiment of the present invention.

As shown in FIG. 13, the correction section 334 is provided with a two-dimensional Fourier transform section 340 and a visual characteristic correction section 342. The two-dimensional Fourier transform section 340 performs a two-dimensional Fourier transform on the specular reflected light-luminance image data $Y_s(x,y)$ to convert the same to a frequency spectrum $F_s(u,v)$ in the spatial frequency domain. The visual characteristic correction section 342 performs correction to match the frequency spectrum $F_s(u,v)$ that has been converted by the two-dimensional Fourier transform section 340 with a human visual frequency characteristic.

Here, the visual characteristic correction section 342 relating to the present embodiment converts the frequency spectrum $F_s(u,v)$ to polar co-ordinates $F_s(f,\theta)$, and multiplies the visual transfer function VTF(f) of the aforementioned equation (2) therewith for each of values of θ to calculate the corrected frequency spectrum $F'_s(f,\theta)$. While equation (2) is employed as the visual transfer function for the present embodiment, various formulas have been proposed as visual transfer functions (for example, Dooley's approximation), and such formulas may be used.

The micro-gloss value calculation section 337 (see FIG. 12) calculates the micro-gloss value MIG, which is a physical quantity corresponding to luminance differences between specular reflected light and diffuse reflected light that are perceived by humans, from the corrected frequency spectrum $F'_s(f,\theta)$ that has been calculated.

Meanwhile, the macro-gloss value calculation section 336 calculates the macro-gloss value MAG, which is a physical quantity corresponding to nonuniformities in luminances of specular reflected light (i.e., a reciprocal of a signal-to-noise ratio) that are perceived by humans, from the corrected frequency spectrum $F'_s(f\theta)$ that has been corrected by the visual characteristic correction section 342 and the diffuse reflected light-luminance image data $Y_d$ that has been calculated by the luminance calculation section 332.

Next, structure of the macro-gloss value calculation section 336 relating to the present embodiment will be described in detail with reference to FIG. 14.

Figure 14:
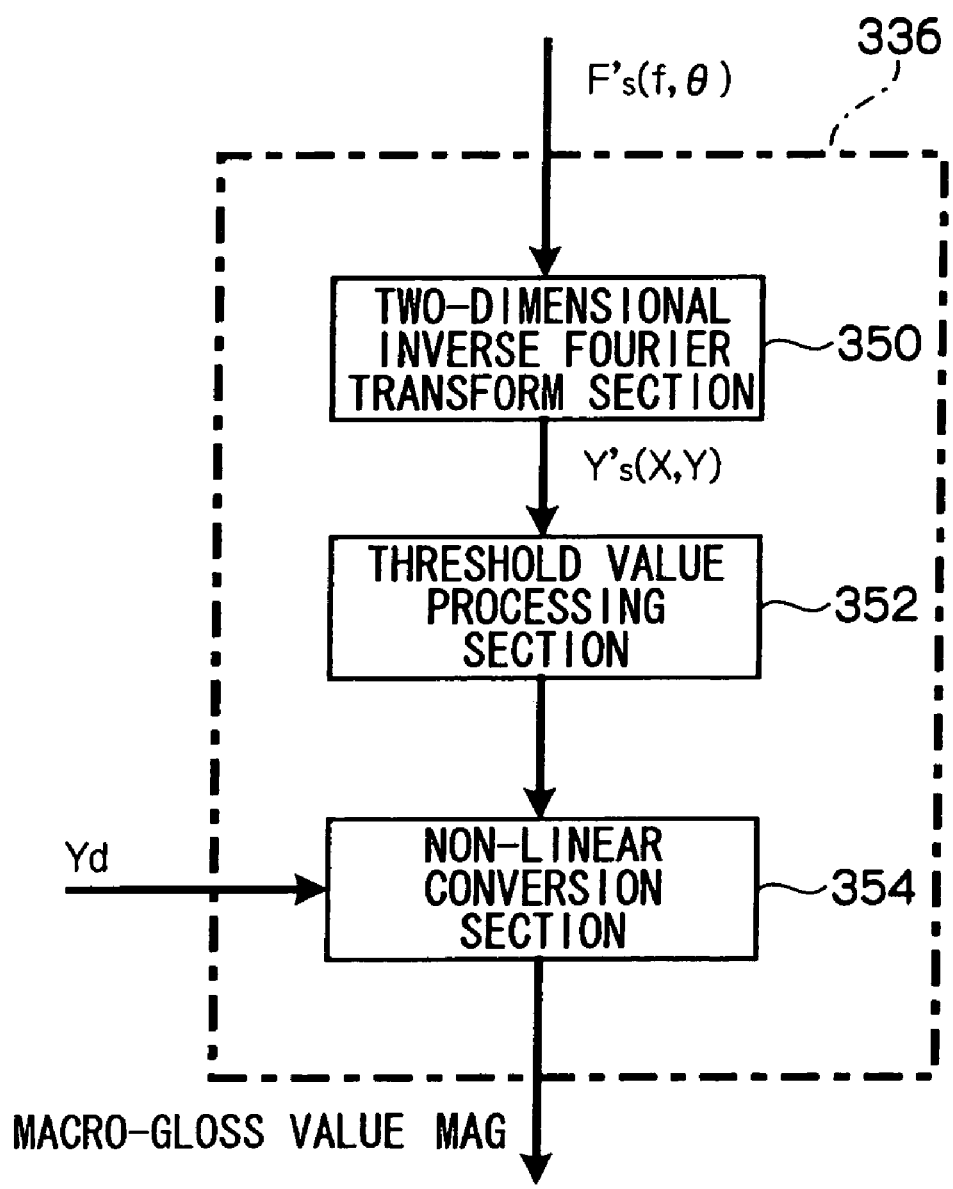
FIG. 14 is a functional block diagram showing detailed structure of a macro-gloss value calculation section relating to the third embodiment of the present invention.

As shown in FIG. 14, the macro-gloss value calculation section 336 is provided with a two-dimensional inverse Fourier transform section 350, a threshold value processing section 352 and a non-linear conversion section 354. The two-dimensional inverse Fourier transform section 350 performs a two-dimensional inverse Fourier transform on the corrected frequency spectrum $F'_s(f,\theta)$, to convert the same to specular reflected light-luminance corrected image data $Y'_s(x,y)$ in the image space domain. The threshold value processing section 352 calculates an average value $Y'_s$high of luminances of pixels, in the specular reflected light-luminance corrected image data $Y'_s(x,y)$ which has been two-dimensional inverse Fourier-transformed, at which the luminance is above a predetermined value. The non-linear conversion section 354 finds an average value $Y_d$ave of luminances of the diffuse reflected light-luminance image data $Y_d(x,y)$, and calculates the macro-gloss value MAG on the basis of this average value $Y_d$ave and the average value $Y'_s$high that has been calculated by the threshold value processing section 352.

Here, the threshold value processing section 352 relating to the present embodiment finds a frequency distribution of luminances in the corrected image data $Y'_s(x,y)$, and calculates the average value $Y'_s$high of luminances at pixels of which the luminance is at or above a middle value (=(a maximum value−a minimum value)/2) of this frequency distribution.

The non-linear conversion section 354 relating to the present embodiment performs a non-linear conversion from the average value $Y'_s$high and the average value $Y_d$ave using the following equation (7) to calculate the macro-gloss value MAG.

$$MAG = 100 \cdot \log(1 + 9 \cdot (Y'_s\text{high} - Y_d\text{ave})) \quad (7)$$

Wherein:

$Y'_s$high is the average value from the middle value of the frequency distribution of the corrected image data $Y'_s(x,y)$ upward; and $Y_d$ave is the average value of the diffuse reflected light-luminance image data $Y_d(x,y)$.

Here, because it is thought that a human perceives overall glossiness by observing high-luminance regions of specular reflected light, in the present embodiment, the predetermined value and above is a region of luminances at and above the middle value of the frequency distribution, which region is extracted by the non-linear conversion section 354. Further, because a relationship between glossinesses that a human senses by vision and luminance differentials between specular reflected light and diffuse reflected light is non-linear, the above-mentioned equation (7) is a non-linear conversion equation in which coefficients of a relational expression between the macro-gloss value MAG and a visual glossiness have been optimized.

Next, structure of the micro-gloss value calculation section 337 relating to the present embodiment will be described in detail with reference to FIG. 15.

Figure 15:
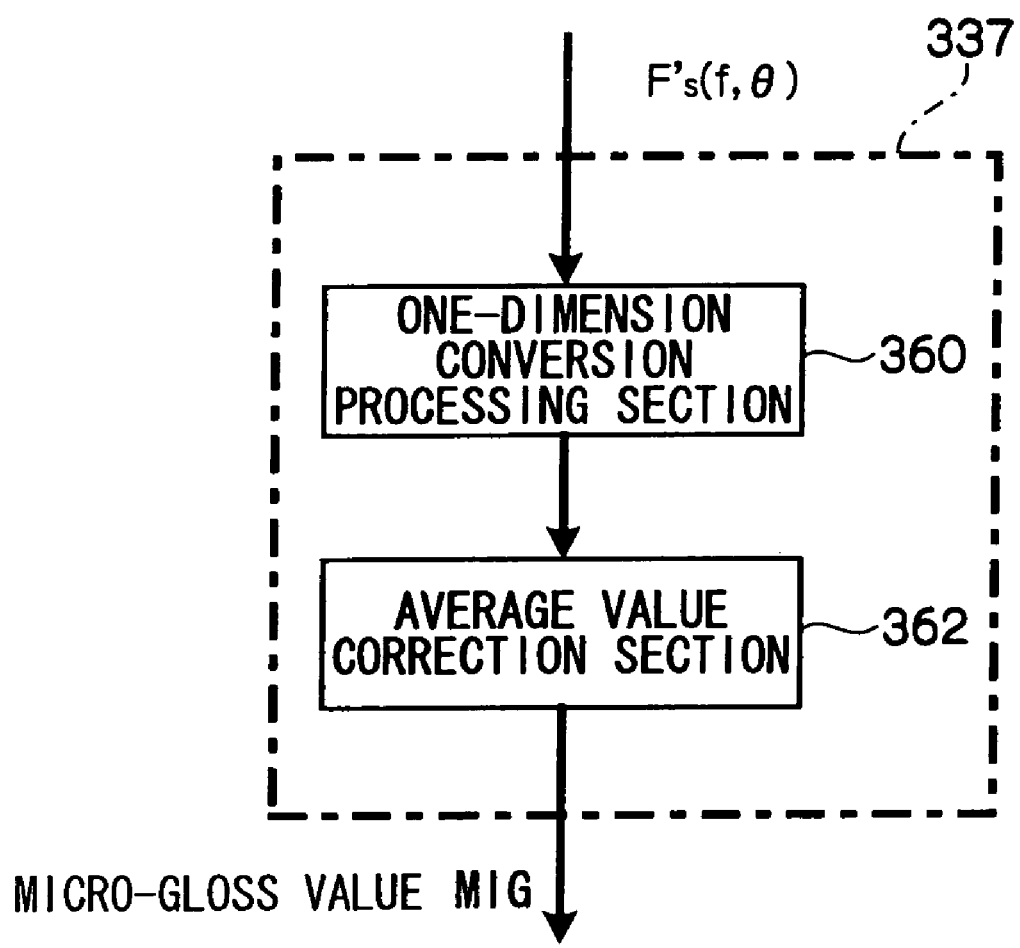
FIG. 15 is a functional block diagram showing detailed structure of a micro-gloss value calculation section relating to the third embodiment of the present invention.

As shown in FIG. 15, a one-dimension conversion processing section 360 and an average value correction section 362 are provided. The one-dimension conversion processing section 360 integrates the corrected frequency spectrum $F'_s(f,\theta)$, which has been corrected by the visual characteristic correction section 342, in the direction of $\theta$ to obtain a one-dimensional frequency spectrum $G'_s(f)$. The average value correction section 362 calculates the micro-gloss value MIG on the basis of the one-dimensional frequency spectrum $G'_s(f)$ and the specular reflected light-luminance image data $Y_s(x,y)$.

The average value correction section 362 relating to the present embodiment integrates the one-dimensional frequency spectrum $G'_s(f)$ that has been found by the one-dimension conversion processing section 360 over all frequencies, as shown in the following equation (8), and divides the integrated integral value by an average value $Y_s$ave of luminances of the specular reflected light-luminance image data to calculate the micro-gloss value MIG.

$$MIG = \int G'_s(f) df / Y_s ave \quad (8)$$

Then, the evaluation value calculation section 338 relating to the present embodiment (see FIG. 12), on the basis of the macro-gloss value MAG calculated by the macro-gloss value calculation section 336 and the micro-gloss value MIG calculated by the micro-gloss value calculation section 337, calculates a gloss evaluation value VG from, for example, a weighted linear sum of the macro-gloss value MAG and the micro-gloss value MIG as shown in the following equation (9).

$$VG = k1 \cdot MAG + k2 \cdot MIG + k3 \quad (9)$$

Here, for the conversion coefficients k1 to k3 in equation (9), optimum values are preparatorily found by multiple regression analysis of subjective glossinesses obtained from sensory evaluation tests and employed. In the present embodiment, k1=0.035, k2=0.059 and k3=0.715.

For the present embodiment, a case in which the gloss evaluation value VG is calculated using equation (9) has been described. However, the present invention is not limited thus and, for example, the following equation (10) or equation (11) may be used.

$$VG = k1 \cdot MAG + k2 \cdot MIG + k3 \cdot MAG \cdot MIG + k4 \quad (10)$$

$$VG = k1 \cdot MAG^{k2} \cdot MIG^{k3} \quad (11)$$

Next, operations of the gloss measurement apparatus 10 relating to the present embodiment will be described.

First, a flow of operation of the gloss measurement apparatus 10 when light reflected from the standard surface 328, which is light emitted from the light source 320, is captured and average values of luminance of the standard surface 328 are stored to the standard information storage section 335 will be briefly described.

At the gloss measurement apparatus 10 relating to the present embodiment, when a user performs predetermined control for instructing a measurement of luminance of the standard surface 328 from a control panel, at a time of apparatus installation or the like, the control section 315 controls the Y-axis driving section 324 to move the stage 302 in the Y direction and controls the X-axis driving section 326 to move the optics section 14 in the X direction, causing the optics section 14 to oppose the standard surface 328. Then, the control section 315 controls the optical system control section 316, a control signal CN1 is outputted from the optical system control section 316 to the halogen fiber light source 320A, and the halogen fiber light source 320A emits light. The light emitted from the light source 320 is reflected by the standard surface 328 and is incident on both the specular reflected light capture section 322 and the diffuse reflected light capture section 323.

The control section 315 controls the image capture system control section 317, and an image of specular reflected light from the standard surface 328, which is imaged onto the CCD area sensor 322B, is captured by the specular reflected light capture section 322 with an exposure time $ET_o$. The specular reflected light capture section 322 outputs the captured specular reflected light image data and exposure time information representing the exposure time $ET_o$ to the image processing section 318. The image processing section 318 stores average values of R, G and B of the specular reflected light image data obtained by the capture and the exposure time $ET_o$ to the standard information storage section 335.

Next, a flow of operation of the gloss measurement apparatus 10 when a measurement of a gloss evaluation value of an image recorded at a recording medium is performed by the gloss measurement apparatus 10 relating to the present embodiment will be described.

In the gloss measurement apparatus 10 relating to the present embodiment, laser light from the laser pointer 327 is outputted to the stage 302 and indicates an image capture position by a spot position on the stage 302. The measurement subject 12 is placed at a predetermined position on the stage 302 by a user, and position adjustment control is performed at a control panel to move a range which is a measurement target of the object to be measured 12 to the spot position on the stage 302. In accordance with this position adjustment control, the control section 315 controls the Y-axis driving section 324 to move the stage 302 in the Y direction and controls the X-axis driving section 326 to move the optics section 14 in the X direction.

Then, in the gloss measurement apparatus 10, when a predetermined control for instructing the start of measurement of the gloss evaluation value VG is performed by a user at the control panel, the control section 315 stops output of the laser light of the laser pointer 327 and controls the optical system control section 316, the control signal CN1 is outputted from the optical system control section 316 to the halogen fiber light source 320A, and the halogen fiber light source 320A emits light. The light emitted from the light source 320 is reflected at the object to be measured 12 and is incident at both the specular reflected light capture section 322 and the diffuse reflected light capture section 323.

Herein, the light-emission of the halogen fiber light source 320A, rather than being implemented by the control signal CN1 from the optical system control section 316, may simply have been turned on when the power of the apparatus was turned on.

The control section 315 controls the image capture system control section 317 and, on the basis of light amounts of light that are incident at the specular reflected light capture section 322 and the diffuse reflected light capture section 323, sets the exposure time $ET_s$ of specular reflected light for the specular reflected light capture section 322 and the exposure time $ET_d$ of diffuse reflected light image data for the diffuse reflected light capture section 323, such that exposure amounts of images that are respectively captured by the specular reflected light capture section 322 and the diffuse reflected light capture section 323 are constant. Then, the control section 315 controls the image capture system control section 317, an image of the specular reflected light from the object to be measured 12 that is imaged onto the CCD area sensor 322B is captured by the specular reflected light capture section 322, with the exposure time $ET_s$, and an image of the diffuse reflected light from the object to be measured 12 that is imaged onto the CCD area sensor 323B is captured by the diffuse reflected light capture section 323, with the exposure time $ET_d$.

The specular reflected light capture section 322 outputs the captured specular reflected light image data and exposure time information representing the exposure time $ET_s$ to the image processing section 318.

Further, the diffuse reflected light capture section 323 outputs the captured diffuse reflected light image data and exposure time information representing the exposure time $ET_d$ to the image processing section 318.

The image processing section 318 stores the specular reflected light image data which has been obtained by capture by the specular reflected light capture section 322 at the specular reflected light image storage section 330, stores the diffuse reflected light image data which has been obtained by capture by the diffuse reflected light capture section 323 at the diffuse reflected light image storage section 331, and stores the exposure time $ET_s$ and the exposure time $ET_d$ at the exposure time storage section 333.

Then, the image processing section 318 performs gloss evaluation value calculation processing, which is described later, on the basis of the specular reflected light image data, the diffuse reflected light image data, and the exposure time $ET_s$ and exposure time $ET_d$, to calculate the gloss evaluation value VG, and outputs the gloss evaluation VG to the display section 19.

Hence, the gloss evaluation value VG of the object to be measured 12 that has been calculated is displayed at the display section 19.

Figure 16A:
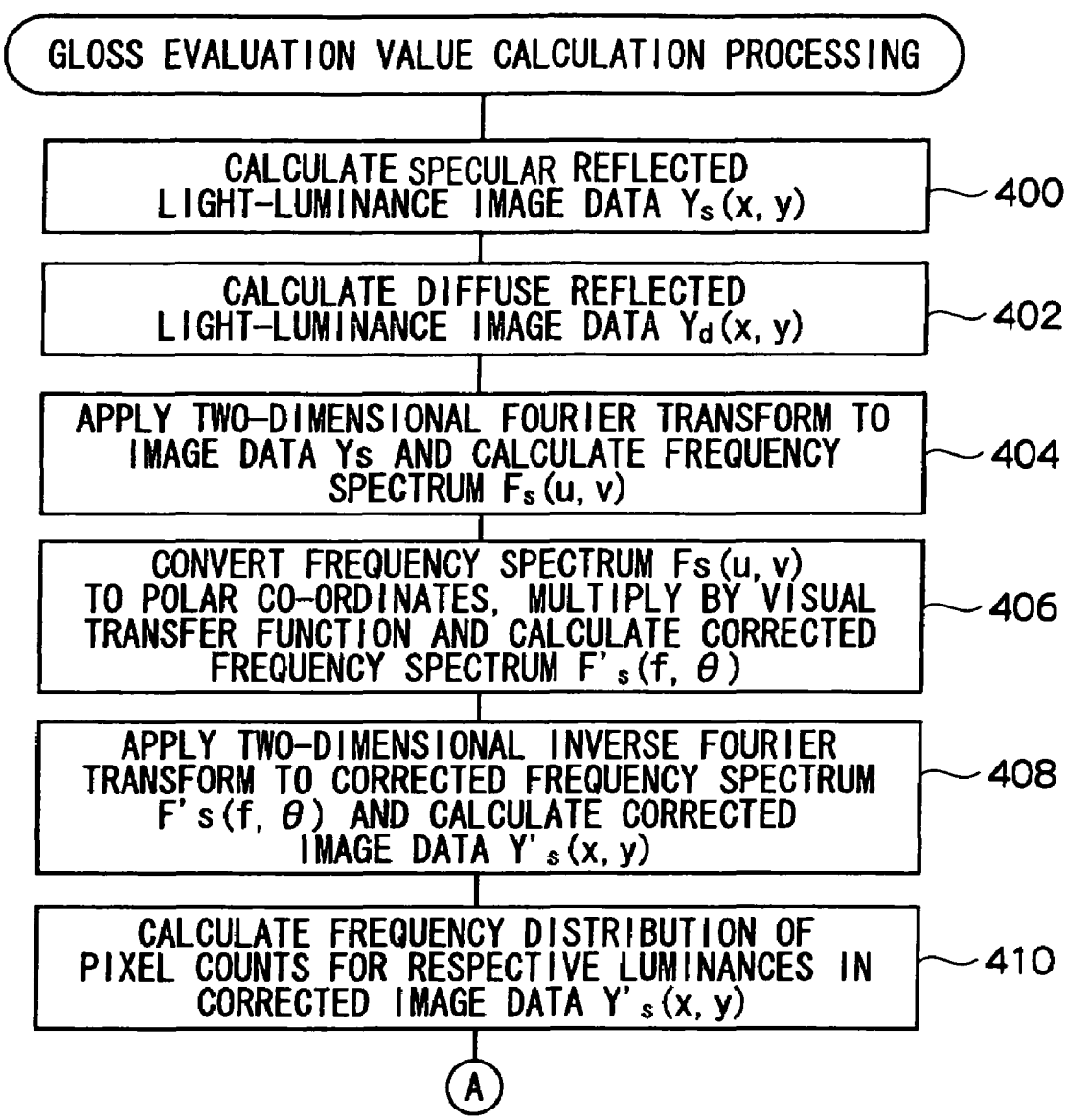
FIGS. 16A and 16B are a flowchart showing a flow of gloss evaluation value calculation processing relating to the third embodiment of the present invention.
Figure 16B:
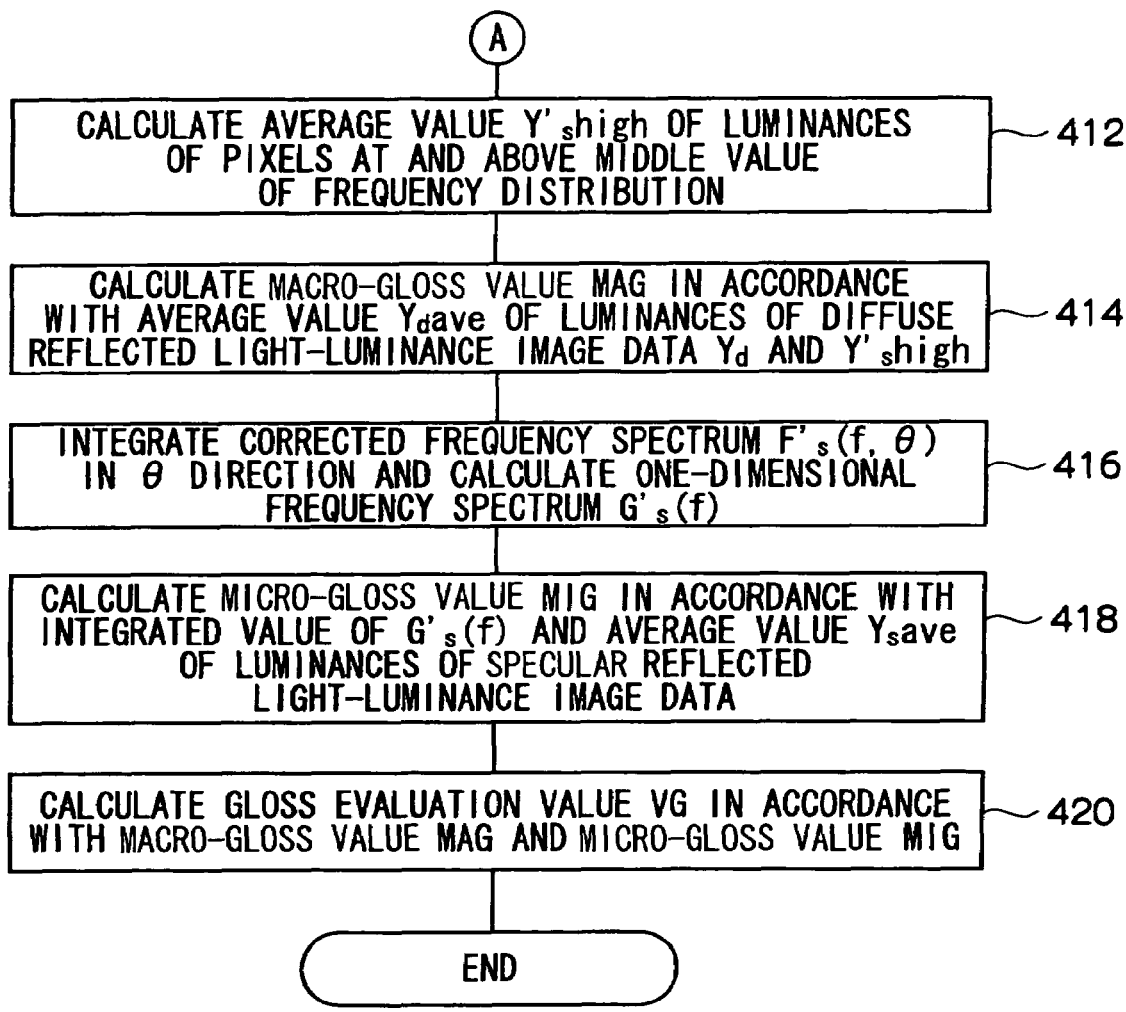

Next, operations of the gloss measurement apparatus 10 when the above-mentioned gloss evaluation value calculation processing is executed will be described with reference to FIGS. 16A and 16B. FIGS. 16A and 16B are a flowchart showing a flow of the gloss evaluation value calculation processing.

In step 400 of FIGS. 16A and 16B, the specular reflected light image data $(R_s(x,y), G_s(x,y), B_s(x,y))$ stored at the specular reflected light image storage section 330, the specular reflected light exposure time $ET_s$ stored at the exposure time storage section 333, and the average values of R, G and B and exposure time $ET_o$ of the specular reflected light image data for the standard surface 328 stored at the standard information storage section 335 are read, and the specular reflected light-luminance image data $Y_s(x,y)$ is calculated using the aforementioned equation (5).

Next, in step 402, the diffuse reflected light image data $(R_d(x,y), G_d(x,y), B_d(x,y))$ stored at the diffuse reflected light image storage section 331, the diffuse reflected light exposure time $ET_d$ stored at the exposure time storage section 333, and the average values of R, G and B and exposure time $ET_o$ of the specular reflected light image data for the standard surface 328 stored at the standard information storage section 335 are read, and the diffuse reflected light-luminance image data $Y_d(x,y)$ is calculated using the aforementioned equation (6).

Next, in step 404, a two-dimensional Fourier transform is applied to the specular reflected light-luminance image data $Y_s(x,y)$ that was calculated in step 400, and the frequency spectrum $F_s(u,v)$ in the spatial frequency domain is calculated.

Then, in step 406, the frequency spectrum $F_s(u,v)$ that has been calculated in the above step 404 is converted to frequency information $F_s(f,\theta)$ in polar co-ordinates, the visual transfer function VTF(f) illustrated in the aforementioned equation (2) is multiplied with the frequency information $F_s(f,\theta)$, and a corrected frequency spectrum $F'_s(f,\theta)$ is calculated.

Next, in step 408, a two-dimensional inverse Fourier transform is applied to the corrected frequency spectrum $F'_s(f,\theta)$ that has been calculated, to convert the same to the corrected image data $Y'_s(x,y)$ of specular reflected light luminances in the image space domain.

Next, in step 410, a frequency distribution of pixel counts for each of luminances in the transformed corrected image data of specular reflected light luminances $Y'_s(x,y)$ is calculated.

Next, in step 412, an average value $Y'_s$high of luminances of pixels at and above the middle value (=(maximum value−minimum value)/2) of the calculated frequency distribution is calculated.

Then, in step 414, the average value $Y_d$ave of the luminances of the diffuse reflected light-luminance image data $Y_d(x,y)$ that was calculated in step 402 is found, and the macro-gloss value MAG is calculated from this average value $Y_d$ave and the luminance average value $Y'_s$high calculated in step 412, using the aforementioned equation (7).

Next, in step 416, the corrected frequency spectrum $F'_s(f,\theta)$ that was calculated in the above step 406 is integrated in the X-direction to obtain a one-dimensional frequency spectrum $G'_s(f)$.

Next, in step 418, the integrated value, into which the one-dimensional frequency spectrum $G'_s(f)$ has been integrated over all frequencies, is divided by the average value $Y_s$ave of luminances of the specular reflected light-luminance image data that was calculated in step 400, to calculate the micro-gloss value MIG.

Next, in step 420, based on the macro-gloss value MAG that was calculated in the above step 414 and the micro-gloss value MIG that was calculated in the above step 418, the gloss evaluation value VG is calculated using the aforementioned equation (9) and outputted to the display section 19. Thereafter, this gloss evaluation value calculation processing ends.

Figure 17A:
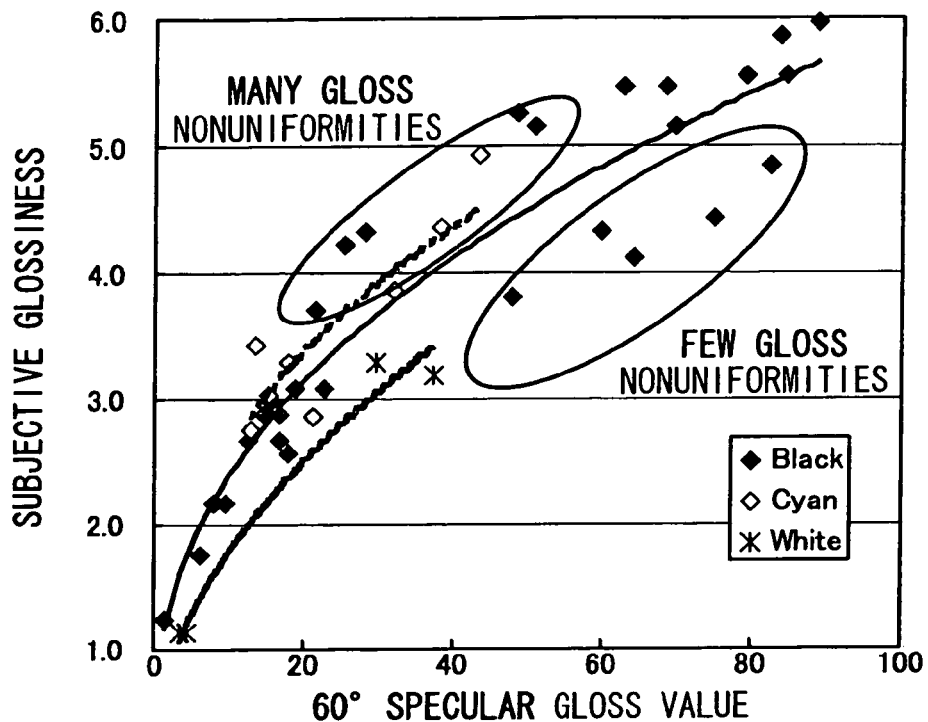
FIGS. 17A and 17B are graphs showing results when gloss values of predetermined objects to be measured are measured by a gloss measurement method relating to the third embodiment of the present invention.
Figure 17B:
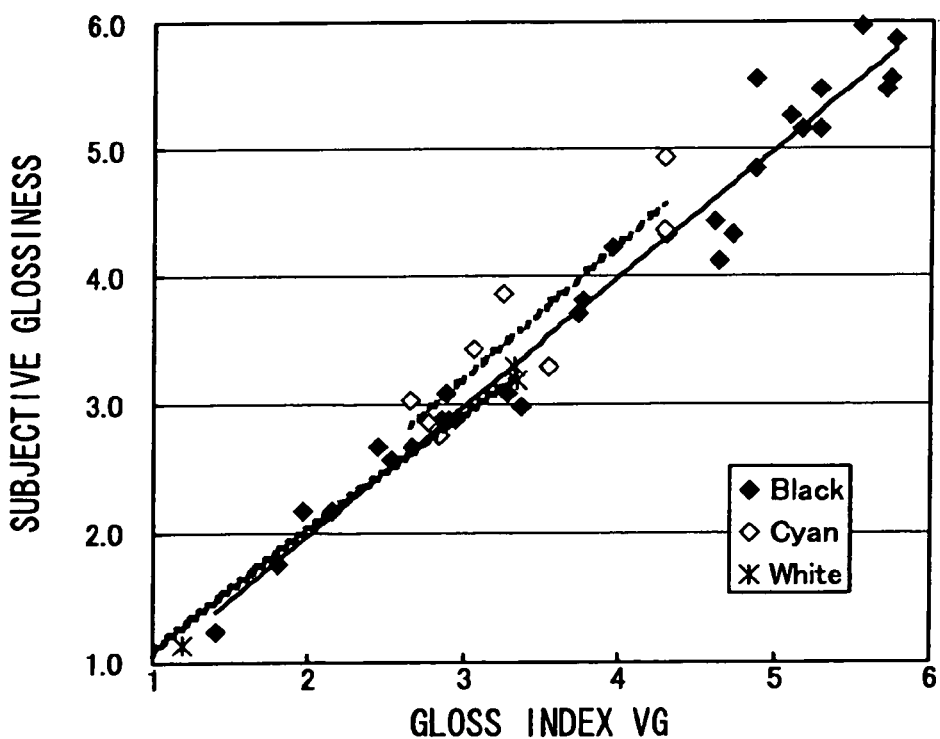

FIGS. 17A and 17B show examples of measurement results of gloss value of matching objects to be measured 12 (herebelow referred to as objects to be measured) by each of the gloss measurement apparatus 10 relating to the third embodiment and the specular gloss measurement method (JIS-Z8741). For FIG. 17A, specular gloss values (herebelow referred to as 60° specular gloss values) are measured by the specular gloss measurement method with the incidence angle on the object to be measured θ=60°, and are shown on the horizontal axis. In FIG. 17B, calculation results for the objects to be measured of gloss evaluation values VG according to the gloss measurement apparatus 10 relating to the present embodiment are shown on the horizontal axis. The vertical axes of FIGS. 17A and 17B are subjective glossinesses obtained by performing sensory evaluation tests with human vision on the same predetermined objects to be measured, and show numerical values for higher subjective glossinesses.

Here, for the present embodiment, the plural objects to be measured which are targets of measurement are prepared and measurements are performed thereon. Images of each of the colors black and cyan are printed by an image-forming apparatus with an electrophotographic system or an inkjet system for the respective objects to be measured. Note that 'white' is the gloss of the paper.

As shown in FIG. 17A, a correlation between the 60° specular gloss values and the subjective glossinesses is low, with a contribution ratio ($R^2$) being 0.802.

Now, as a result of the assiduous investigations by the present inventors, it has been found that factors which reduce a contribution ratio between specular gloss values measured by the specular gloss measurement method and subjective glossinesses include discrepancies in gloss nonuniformities of the objects to be measured 12, linearity of subjective glossinesses and discrepancies in colors of measured regions of the objects to be measured 12.

Thus, for example, as shown in FIG. 17A, among the 60° specular gloss values, if there are many gloss nonuniformities, there will tend to be a lower specular gloss value even for subjective glossinesses which are the same, or there will tend to be a higher subjective glossiness even for specular gloss values which are the same. Further, because a relationship of subjective glossinesses is non-linear, correlation over a broad range of gloss from low gloss to high gloss is weaker. Correlation tendencies also differ because of discrepancies in colors of the objects to be measured 12.

In contrast, FIG. 17B shows measurement results according to the gloss measurement apparatus 10 relating to the present embodiment. The correlation between the gloss indexes VG and the subjective glossinesses is high, with the contribution ratio ($R^2$) being 0.960.

Thus, in the gloss measurement apparatus 10 relating to the third embodiment, the optical system of the measuring apparatus is made to be close to observation conditions in ordinary offices, and a gloss index is calculated from a weighted linear sum of a macro-gloss value and a micro-gloss value. Therefore, even if there are nonuniformities in gloss at the object to be measured 12, it is possible to obtain a result which attains correspondence with a human subjective glossiness. Further, because image capture is performed with an exposure time being altered in accordance with brightness of a measurement target region and light amounts of each of R, G and B that are obtained by the image capture being divided by the exposure time to calculate luminances, an apparent dynamic range is broadened and it is possible to calculate luminances regardless of brightness of the measurement target region. Further still, because a non-linear transformation of the calculated luminances is applied, even if the object to be measured has a wide range of gloss, an evaluation value which attains correspondence with a subjective glossiness can be calculated. Further yet, because diffuse reflected light is captured and the evaluation value is corrected in accordance with the diffuse reflected light image data that is obtained, even if the object to be measured 12 has a variety of colors, it is possible to calculate an evaluation value which attains correspondence with the subjective glossiness.

According to the third embodiment as described above, a gloss measurement apparatus emits light from a light source and finds an evaluation value representing glossiness of an object to be measured on the basis of specular reflected light which is reflected by the object to be measured. A specular reflection image acquisition component (here, the specular reflected light capture section 322) acquires specular reflected light image information in accordance with received light amounts at respective predetermined pixels of specular reflected light from a surface of an object to be measured. A diffuse reflection image acquisition component (here, the diffuse reflected light capture section 323) acquires diffuse reflected light image information in accordance with received light amounts at respective predetermined pixels of diffuse reflected light which has been emitted from the light source and diffusely reflected by the surface of the object to be measured. A calculation component (here, the image processing section 318) calculates the evaluation value representing glossiness of the object to be measured on the basis of the specular reflected light image information acquired by the specular reflection image acquisition component and the diffuse reflected light image information acquired by the diffuse reflection image acquisition component. Thus, even if there are nonuniformities in gloss at the object to be measured, it is possible to calculate an evaluation value which attains correspondence with a subjective glossiness.

Further, according to the third embodiment, the light source emits light which includes a predetermined incidence angle deviation about an optical axis of the light that is incident on the surface of the object to be measured. Thus, it is possible for an optical system to approach observation conditions in ordinary offices in measuring the gloss value.

Further, according to the third embodiment, the calculation component includes a luminance calculation component (here, the luminance calculation section 332), a first physical quantity calculation component (here, the macro-gloss value calculation section 336), a second physical quantity calculation component (here, the micro-gloss value calculation section 337) and an evaluation value calculation component (here, the evaluation value calculation section 338). The luminance calculation component calculates specular reflected light luminances of the respective pixels on the basis of the received light amounts of the respective pixels represented by the specular reflected light image information, and calculates diffuse reflected light luminances of the respective pixels on the basis of the received light amounts of the respective pixels represented by the diffuse reflected light image information. The first physical quantity calculation component calculates a first physical quantity, which corresponds to a luminance difference between the specular reflected light and the diffuse reflected light, (here, the macro-gloss value MAG) on the basis of the specular reflected light and diffuse reflected light luminances calculated by the luminance calculation component. The second physical quantity calculation component calculates a second physical quantity, which corresponds to nonuniformities in luminance of the specular reflected light, (here, the micro-gloss value MIG) on the basis of the specular reflected light luminances calculated by the luminance calculation component. The evaluation value calculation component calculates an evaluation value representing glossiness of the object to be measured by multiplying the first physical quantity and the second physical quantity with respective predetermined weighting coefficients and finding a linear sum of the values that are thus obtained. Thus, even if there are nonuniformities in gloss at the object to be measured 12, it is possible to obtain a value which attains correspondence with the subjective glossiness, and even if the object to be measured 12 features various colors, it is possible to calculate an evaluation value which attains correspondence with the subjective glossiness.

Further, according to the third embodiment, the luminance calculation component divides the received light amounts of the respective pixels represented by the specular reflected light image information by a light-receiving time of the specular received light (here, the exposure time $ET_s$), and calculates the specular reflected light luminances on the basis of the received light amounts per unit time that are obtained, and the luminance calculation component divides the received light amounts of the respective pixels represented by the diffuse reflected light image information by a light-receiving time of the diffuse received light (here, the exposure time $ET_d$), and calculates the diffuse reflected light luminances on the basis of the received light amounts per unit time that are obtained. Thus, an apparent dynamic range can be broadened, such that it is possible to attain a signal-to-noise ratio even if the object to be measured features a broad range of gloss from low gloss to high gloss, and to attain correspondence with a subjective glossiness.

Further, according to the third embodiment, a standard surface luminance storage component (here, the standard information storage section 335) is further provided, which stores a luminance of specular reflected light at a standard surface which is used in measurement of specular gloss (here, the standard surface 328). The luminance calculation component calculates the specular reflected light luminances of respective pixels and the diffuse reflected light luminances of respective pixels as values which are normalized in accordance with the luminance of specular reflected light at the standard surface. Thus, it is possible to measure gloss value with reference to the standard surface.

Further, according to the third embodiment, the first physical quantity calculation component calculates an average value of luminances of respective pixels that are at and above a middle value between a maximum luminance and a minimum luminance, of the specular reflected light luminances of the respective pixels, and calculates the first physical quantity on the basis of this average value and an average value of the diffuse reflected light luminances of the respective pixels. Thus, a first physical quantity attaining a correlation with human vision can be calculated.

Further, according to the third embodiment, the second physical quantity calculation component converts the specular reflected light luminances at respective pixels to luminances in the spatial frequency domain by applying a two-dimensional Fourier transform thereto, and divides an integrated value, into which the thus obtained specular reflected light luminances at respective pixels in the spatial frequency domain are integrated over all frequencies, by an average value of the specular reflected light luminances at the respective pixels to calculate the second physical quantity. Thus, it is possible to appropriately calculate a second physical quantity which corresponds to nonuniformities in luminance of specular reflected light of the respective pixels.

Further, according to the third embodiment, a stage, a first translation component (here, the X-axis driving section 326), and a second translation component (here, the Y-axis driving section 324) are further provided. The stage includes a stage surface which retains the object to be measured. The first translation component translates the light source, the specular reflection image information acquisition component and the diffuse reflection image information acquisition component in a predetermined direction which is parallel with the stage surface (here, the X direction). The second translation component translates the stage in a direction intersecting the predetermined direction. Thus, it is possible to measure a lateral range of the object to be measured 12 at high speed in a compact space.

Further, according to the third embodiment, the stage is formed as an electrostatic adherence plate which adheres and retains the object to be measured by electrostatic force. Thus, the object to be measured which is a measurement target can be stably retained.

Further, according to the third embodiment, a laser output component (here, the laser pointer 327) is further provided, which outputs laser light to an incidence position at the stage surface of the light that is emitted from the light source. Thus, it is possible to easily position a region of gloss measurement of the object to be measured 12 at a measurement position.

Further, according to the third embodiment, the light source includes a halogen fiber light source, which emits light, and a condensing lens, which focuses the light emitted from the halogen fiber light source. Thus, it is possible to concentrate the light that is outputted from the halogen fiber light source and obtain large light amounts. Furthermore, the light source includes a diffuser which diffuses the light that has been focused by the condensing lens. Thus, it is possible to alter an incidence angle deviation of the light with respect to the optical axis, by altering a diffusion angle of the diffuser.

Figure 18:
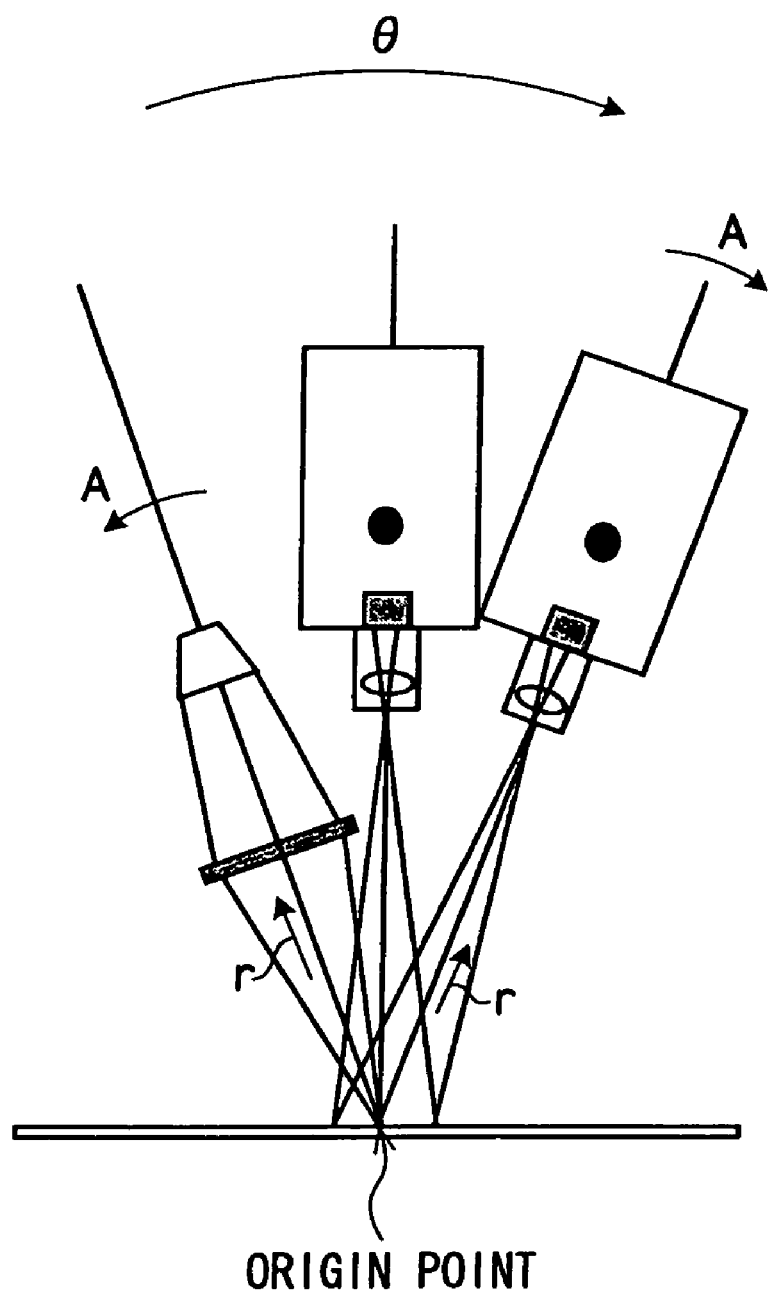
FIG. 18 is a diagram for description of movement directions of a light source, a specular reflected light capture section and a diffuse reflected light capture section.

Anyway, for the gloss measurement apparatus 10 relating to the third embodiment, a case has been described in which an angle about the normal line N between the light source 320 and the specular reflected light capture section 322 is 40°. However, the present invention is not limited thus. It is also possible to alter the position of the light source 320 and alter the incidence angle θ of the light that is emitted at the object to be measured 12 from the light source 320, and to dispose a position of the specular reflected light capture section 322 on an optical axis of specular reflected light of the light that is incident at the incidence angle θ, to alter an angle that is formed between the light source 320 and the specular reflected light capture section 322 about the normal line N. Furthermore, it is possible to further provide, for example, an angle alteration mechanism which, as shown in FIG. 18, moves the light source 320 and the specular reflected light capture section 322 in the respective directions of arrows A, with an incidence position on the stage 302 of the light that is emitted from the light source 320 serving as an origin point, so as to alter the angle about the normal line N that is formed between the light source 320 and the specular reflected light capture section 322. With the angle alteration mechanism, it is possible to reduce an angle that is formed when measuring the object to be measured 12 for a high gloss and to increase an angle that is formed when measuring the object to be measured 12 for a low gloss, and thus to accurately measure evaluation values of glossiness.

Moreover, as shown in FIG. 18, the gloss measurement apparatus 10 relating to the third embodiment may be provided with an redirection movement mechanism which moves the light source 320, the specular reflected light capture section 322 and the diffuse reflected light capture section 323 in a radial redirection, with an incidence position at the stage 302 of light that is emitted from the light source 320 serving as an origin point of polar-co-ordinates. By moving the light source 320 in the redirection, it is possible to alter the incidence angle deviation 325. Further, even if a focusing length changes because of a change of the focusing lens 322A, it is possible to acquire a sharp image by suitably moving the specular reflected light capture section 322 and the diffuse reflected light capture section 323 in the redirection. Further still, a θ-direction rotation mechanism may be further provided, which rotates the light source 320, the specular reflected light capture section 322 and the diffuse reflected light capture section 323 as a whole in the direction of a rotation angle θ. Thus, even if a surface of the object to be measured 12 that is retained at the stage 302 is inclined with respect to the stage surface, it is possible to capture the reflected light that has been emitted from the light source 320 with the specular reflected light capture section 322, by rotating the light source 320, the specular reflected light capture section 322 and the diffuse reflected light capture section 323 in the θ-direction.

A normal direction movement mechanism may also be provided, which moves the light source 320, the specular reflected light capture section 322 and the diffuse reflected light capture section 323 relatively in the normal direction N with respect to the stage 302. Thus, if a thickness of the object to be measured 12 is large, it is possible, by relatively moving the specular reflected light capture section 322 and diffuse reflected light capture section 323 and the stage 302 in the normal direction N by an amount corresponding to a thickness of the stage 302 and the object to be measured 12, to excellently capture, of light which has been emitted from the light source 320, the specular reflected light that has been regularly reflected by the surface of the object to be measured 12 with the specular reflected light capture section 322, and it is also possible to excellently capture diffuse reflected light which has been diffusely reflected by the surface of the object to be measured 12 with the diffuse reflected light capture section 323.

EXAMPLE

For an Example, another example of calculating an evaluation value representing glossiness of an object to be measured on the basis of specular reflected light image data and diffuse reflected light image data will be described.

Figure 19:
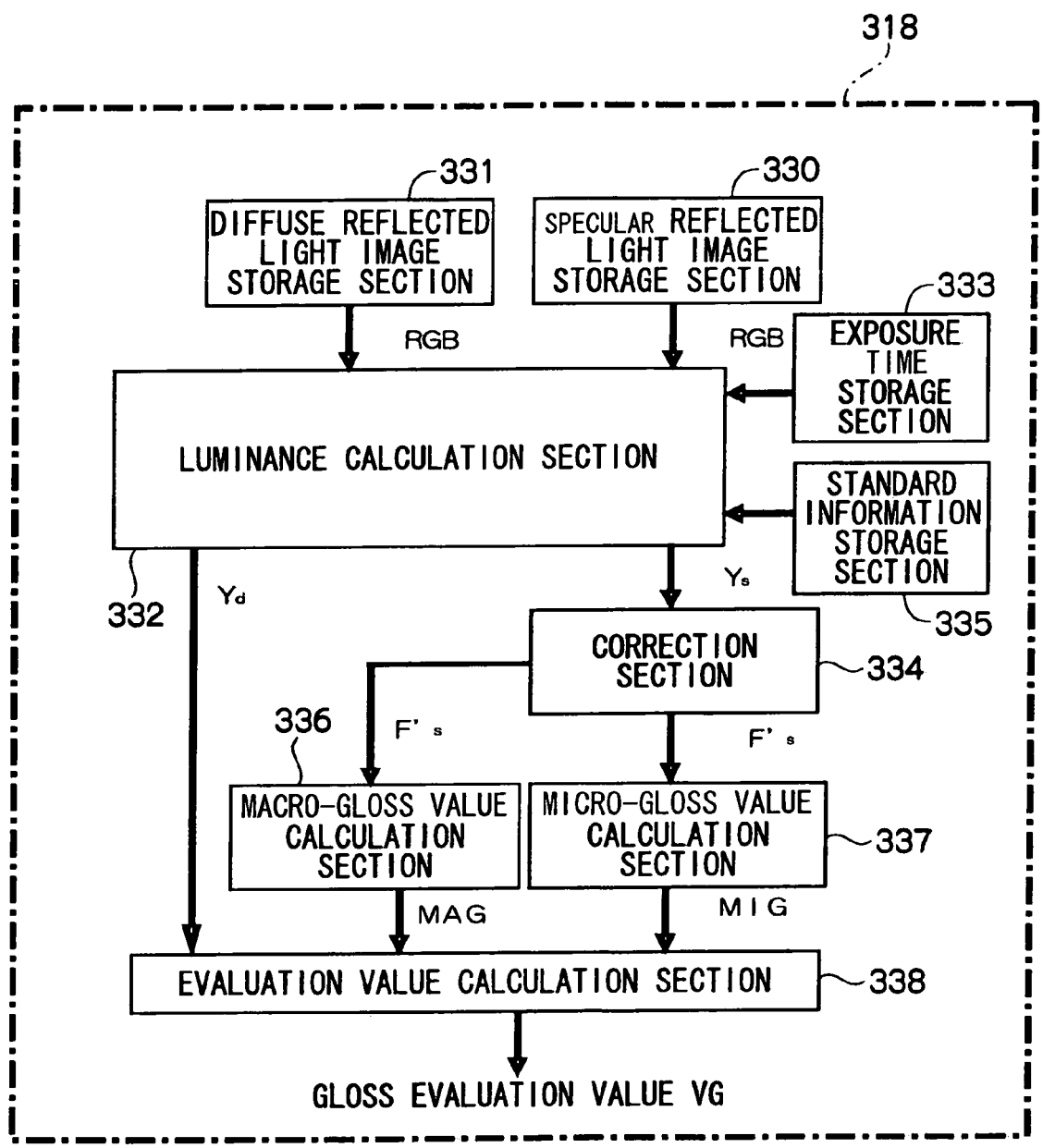
FIG. 19 is a functional block diagram showing detailed structure of an image processing section relating to an Example.

FIG. 19 shows detailed structure of the image processing section 318 in relation to the Example.

The image processing section 318 relating to this example is the same as in the third embodiment, except that factors that are input to the macro-gloss value calculation section 336 and the evaluation value calculation section 338 differ from in the image processing section 318 relating to the third embodiment.

The non-linear conversion section 354 of the macro-gloss value calculation section 336 (see FIG. 14) relating to the Example performs a non-linear conversion from the average value $Y_d$ave using the following equation (12), and calculates the macro-gloss value MAG Equation (12) is equivalent to an equation in which the average value of luminance $Y_d$ave has been removed from the equation (7) that is applied by the macro-gloss value calculation section 336 relating to the third embodiment.

$$MAG = 100 \cdot \log(1 + 9 \cdot (Y'_s \text{high})) \quad (12)$$

The evaluation value calculation section 338 relating to the example (see FIG. 19) calculates a gloss evaluation value VG from the following equation (13) on the basis of the diffuse reflected light luminances $Y_d$, the macro-gloss value MAG and the micro-gloss value MIG $$VG = k1 \cdot MAG + (k2 + k3 - MAG) \cdot Y_d \text{ave} + k4 - MIG + k5 \quad (13)$$

Here, for the conversion coefficients k1 to k5 in equation (13), optimum values are preparatorily found by multiple regression analysis of subjective glossinesses obtained from sensory evaluation tests and employed. Thus, with the image processing section 318 relating to the Example too, evaluation values which attain correspondence with subjective glossinesses can be calculated even if there are nonuniformities in gloss at the objects to be measured.

Herein, the image processing section 318 relating to the third embodiment has been described for a case of calculating specular reflected light-luminance image data $Y_s(x,y)$ and diffuse reflected light-luminance image data $Y_d(x,y)$ from the specular reflected light image data $(R_s(x,y), G_s(x,y), B_s(x,y))$ and the diffuse reflected light image data $(R_d(x,y), G_d(x,y), B_d(x,y))$. However, the present invention is not limited thus. For example, the luminance values may be calculated from tristimulus values X, Y, Z or CIELAB color values L*, a*, b* of the respective pixels of the image. In such cases, similar effects to the present embodiment can be achieved.

Further, for the third embodiment, a case of calculating, at the threshold value processing section 352, an average value $Y'_s$high of luminances of pixels at and above the middle value of the frequency distribution of luminances of the corrected image data $Y'_s(x,y)$ has been described. However, the present invention is not limited thus. A range of pixel numbers for calculating $Y'_s$high may be suitably altered to, for example, a predetermined proportion (for example, 30%) of a total number of pixels from the side of high gloss value, a predetermined number of pixels (for example, 100 pixels) from the side of high gloss value, or the like. In such cases, similar effects to the present embodiment can be achieved.

Further yet, at the gloss measurement apparatus 10 relating to the third embodiment and the Example, the respective functions illustrated for the luminance calculation section 332, the correction section 334, the macro-gloss value calculation section 336, the micro-gloss value calculation section 337 and the evaluation value calculation section 338 may be implemented by software.

Moreover, structures of the gloss measurement apparatus 10 described for the present embodiments (see FIGS. 1 to 3, 6, 10, 11, 18 and 19) are examples, and can be suitably modified within a scope not departing from the spirit of the present invention.

Furthermore, flows of gloss evaluation value calculation processing described for the present embodiments (see FIGS. 4, 7, 16A and 16B) are examples, and can be suitably modified within a scope not departing from the spirit of the present invention.

A first aspect of the present invention is a gloss measurement apparatus for emitting light from a light source and finding an evaluation value, which represents a glossiness of an object to be measured, on the basis of specular reflected light which is reflected by the object to be measured, the gloss measurement apparatus including: an acquisition component, which acquires image information in accordance with received light amounts, at predetermined respective pixels, of specular reflected light from a surface of the object to be measured; a pixel gloss value calculation component, which calculates gloss values of the respective pixels on the basis of the received light amounts of the respective pixels of the image information acquired by the acquisition component; and an evaluation value calculation component, which calculates the evaluation value representing glossiness of the object to be measured on the basis of the gloss values calculated by the pixel gloss value calculation component.

In the first aspect, the image information is acquired by the acquisition component in accordance with received light amounts, at the respective predetermined pixels, of the light regularly reflected from the surface of the object to be measured. Herein, the acquisition of image information by the acquisition component can include, beside acquisition based on received light amounts at respective predetermined pixels of specular reflected light that has been reflected by an object to be measured, acquisition by reading image information stored at a storage medium, acquisition (input) from an external device via a communication circuit such as a LAN, the Internet, an intranet or the like, and the like.

Then, in the present invention, the gloss values of the respective pixels are calculated by the pixel gloss value calculation component on the basis of the received light amounts at the respective pixels of the image information that has been acquired by the acquisition component, and the evaluation value representing the glossiness of the object to be measured is calculated by the evaluation value calculation component on the basis of the gloss values calculated by the pixel gloss value calculation component.

Thus, according to the first aspect, gloss values of respective pixels are calculated on the basis of received light amounts at respective pixels of the acquired image information, and the evaluation value representing the glossiness of the object to be measured is calculated on the basis of the calculated gloss values. Thus, even if there are nonuniformities in gloss at the object to be measured, it is possible to calculate an evaluation value which attains correspondence with a subjective glossiness.

Now, the evaluation value calculation component of the first aspect may include a distribution calculation component, which calculates a distribution of pixel counts for respective gloss values from the gloss values of the respective pixels, and the evaluation value calculation component may identify a gloss value at which a number of pixels, which is summed from a side of high gloss value in the distribution calculated by the distribution calculation component, reaches a predetermined number, and calculate the evaluation value representing glossiness of the object to be measured on the basis of an total gloss value, which is a sum of gloss values of the respective pixels at and above the identified gloss value.

Further, the evaluation value calculation component of the first aspect may include an index value calculation component which, on the basis of the gloss values of the respective pixels, calculates an average gloss index value representing an average value of gloss values of all the pixels and a gloss nonuniformity index value representing a degree of occurrence of gloss nonuniformities, and the evaluation value calculation component may calculate the evaluation value representing glossiness of the object to be measured by multiplying the average gloss index value and the gloss nonuniformity index value with respective predetermined weighting coefficients, and finding a linear sum of values obtained by the multiplication, such that the evaluation value representing glossiness of the object to be measured is larger when the average gloss index value is larger and the evaluation value representing glossiness of the object to be measured is larger when the gloss nonuniformity index value is larger.

It is preferable if the gloss nonuniformity index value is a value found by dividing a standard deviation value of the gloss values of the respective pixels by the average gloss index value.

Further, the present invention may further include a correction component, which performs a correction to cause a spatial frequency characteristic of the gloss values of respective pixels which have been calculated by the pixel gloss value calculation component to correspond with a spatial frequency characteristic of human vision, with the evaluation value calculation component calculating the evaluation value representing glossiness of the object to be measured on the basis of the gloss values of respective pixels which have been corrected by the correction component.

Further, the correction component may be structured to include: a two-dimensional Fourier transform component, which applies a two-dimensional Fourier transformation to the gloss values of the respective pixels which have been calculated by the pixel gloss calculation component, for converting the gloss values to gloss values in a spatial frequency domain; a multiplication component, which multiplies a predetermined visual transfer function, which corresponds to the spatial frequency characteristic of human vision, with frequency information representing the gloss values of the respective pixels which have been converted to spatial frequency domain gloss values by the two-dimensional Fourier transform component; and a two-dimensional inverse Fourier transform component, which applies a two-dimensional inverse Fourier transformation to results of the multiplication by the multiplication component, for converting the multiplication results to gloss values of respective pixels which are pixels in an image space domain.

A second aspect of the present invention is a gloss measurement method for emitting light from a light source and finding an evaluation value, which represents a glossiness of an object to be measured, on the basis of specular reflected light which is reflected by the object to be measured, the method including: acquiring image information in accordance with received light amounts, at predetermined respective pixels, of specular reflected light from a surface of the object to be measured; calculating gloss values of the respective pixels on the basis of the received light amounts of the respective pixels of the acquired image information; and calculating the evaluation value representing glossiness of the object to be measured on the basis of the calculated gloss values.

Accordingly, the second aspect, by operations similar to the first aspect, can calculate an evaluation value that attains correspondence with a subjective glossiness even if there are nonuniformities in gloss at the object to be measured, similarly to the first aspect.

A third aspect of the present invention is a gloss measurement apparatus for emitting light from a light source and finding an evaluation value, which represents a glossiness of an object to be measured, on the basis of specular reflected light which is reflected by the object to be measured, the gloss measurement apparatus including: a specular reflection image information acquisition component, which acquires specular reflected light image information in accordance with received light amounts, at predetermined respective pixels, of specular reflected light from a surface of the object to be measured; and a calculation component, which calculates the evaluation value representing glossiness of the object to be measured on the basis of the specular reflected light image information acquired by the specular reflection image information acquisition component.

In the third aspect, the specular reflected light image information is acquired by the specular reflection image information acquisition component in accordance with the received light amounts at the respective predetermined pixels of regularly reflected light from the surface of the object to be measured. Here, the acquisition of specular reflected light image information by the specular reflection image information acquisition component can include, beside acquisition based on received light amounts at respective predetermined pixels of specular reflected light that has been reflected by an object to be measured, acquisition by reading image information stored at a storage medium, acquisition (input) from an external device via a communication circuit such as a LAN, the Internet, an intranet or the like, and the like.

Then, in the present invention, the evaluation value representing the glossiness of the object to be measured is calculated by the calculation component on the basis of the specular reflected light image information acquired by the specular reflection image information acquisition component.

Thus, according to the third aspect, the specular reflected light image information is acquired in accordance with the received light amounts, at the respective predetermined pixels, of the specular reflected light which has been regularly reflected by the surface of the object to be measured, and the evaluation value representing the glossiness of the object to be measured is calculated on the basis of the acquired specular reflected light image information. Thus, even if there are nonuniformities in gloss at the object to be measured, it is possible to calculate an evaluation value that attains correspondence with a subjective glossiness.

Anyway, the third aspect may further include a diffuse reflection image information acquisition component, which acquires diffuse reflected light image information in accordance with received light amounts, at predetermined respective pixels, of diffuse reflected light which, of the light emitted from the light source, has been diffusely reflected by the surface of the object to be measured, with the calculation component calculating the evaluation value representing glossiness of the object to be measured on the basis of the specular reflected light image information acquired by the specular reflection image information acquisition component and the diffuse reflected light image information acquired by the diffuse reflection image information acquisition component. Here, the acquisition of diffuse reflected light image information by the diffuse reflection image information acquisition component can include, beside acquisition based on received light amounts at the respective predetermined pixels of diffuse reflected light that has been reflected by the object to be measured, acquisition by reading image information stored at a storage medium, acquisition (input) from an external device via a communication circuit such as a LAN, the Internet, an intranet or the like, and the like.

It is preferable if the light source emits light including a predetermined incidence angle deviation about an optical axis of the light that is incident at the surface of the object to be measured.

The calculation component may include: a luminance calculation component, which calculates luminances of specular reflected light at respective pixels on the basis of the received light amounts of the respective pixels represented by the specular reflected light image information, and calculates luminances of diffuse reflected light at respective pixels on the basis of the received light amounts of the respective pixels represented by the diffuse reflected light image information; a first physical quantity calculation component, which calculates a first physical quantity, which corresponds to a luminance difference between specular reflected light and diffuse reflected light, on the basis of the specular reflected light and diffuse reflected light luminances calculated by the luminance calculation component; a second physical quantity calculation component, which calculates a second physical quantity, which corresponds to nonuniformities in luminance of the specular reflected light, on the basis of the specular reflected light luminances calculated by the luminance calculation component; and an evaluation value calculation component, which calculates the evaluation value representing glossiness of the object to be measured, by multiplying the first physical quantity and the second physical quantity with respective predetermined weighting coefficients and finding a linear sum of values obtained by the multiplication.

The luminance calculation component may divide the received light amounts of the respective pixels represented by the specular reflected light image information by a light-receiving time of the specular received light, and calculate the specular reflected light luminances on the basis of received light amounts per unit time that are obtained by this division, and may divide the received light amounts of the respective pixels represented by the diffuse reflected light image information by a light-receiving time of the diffuse received light, and calculate the diffuse reflected light luminances on the basis of received light amounts per unit time that are obtained by this division.

The third aspect may further include a standard surface luminance storage component, which stores a luminance of specular reflected light at a standard surface which is used in measurement of specular gloss, with the luminance calculation component calculating the specular reflected light luminances of respective pixels and the diffuse reflected light luminances of respective pixels as values which are normalized in accordance with the luminance of specular reflected light at the standard surface. Here, the standard surface luminance storage component can include semiconductor memory such as RAM, flash memory or the like, portable memory such as a compact flash, an xD picture card or the like, a fixed storage device such as a hard disk or the like, or an external storage device provided at a server computer or the like which is connected to a network.

The first physical quantity calculation component may calculate an average value of luminances of respective pixels that are at and above a middle value between a maximum luminance and a minimum luminance, of the specular reflected light luminances of respective pixels, and calculate the first physical quantity on the basis of this average value and an average value of the diffuse reflected light luminances of the respective pixels.

The second physical quantity calculation component may apply a two-dimensional Fourier transformation to the specular reflected light luminances at the respective pixels for converting the luminances to luminances in the spatial frequency domain, and divide an integrated value, into which the thus obtained specular reflected light luminances at respective pixels in the spatial frequency domain are integrated over all frequencies, by an average value of the specular reflected light luminances at the respective pixels, for calculating the second physical quantity.

The third aspect may further include: a stage, which includes a stage surface which retains the object to be measured; a first translation component, which translates the light source, the specular reflection image information acquisition component and the diffuse reflection image information acquisition component in a predetermined direction, which is parallel with the stage surface; and a second translation component, which translates the stage in a direction intersecting the predetermined direction.

The third aspect may further include an angle alteration component, which alters an angle that is formed between the light source and the specular reflection image information acquisition component about a normal line from an incidence position on the stage surface of the light emitted from the light source.

The third aspect may further include: a stage, which includes a stage surface which retains the object to be measured; an r-direction movement component, which moves the light source, the specular reflection image information acquisition component and the diffuse reflection image information acquisition component in a radial redirection of polar-co-ordinates, an origin point of which is an incidence position on the stage surface of the light emitted from the light source; and a θ-direction rotation component, which rotates the light source, the specular reflection image information acquisition component and the diffuse reflection image information acquisition component in a rotation angle θ-direction.

The third aspect may further include a normal direction movement component, which relatively moves the light source, the specular reflection image information acquisition component and the diffuse reflection image information acquisition component in a normal direction of the stage surface with respect to the stage.

The stage may be an electrostatic adherence plate which adheres and retains the object to be measured by electrostatic force.

The third aspect may further include a laser output component, which outputs laser light to an incidence position on the stage surface of the light emitted from the light source.

The light source may include: a halogen fiber light source, which emits light; a condensing lens, which condenses the light emitted from the halogen fiber light source; and a diffuser, which diffuses the light that has been condensed by the condensing lens.

A fourth aspect of the present invention is a gloss measurement method for emitting light from a light source and finding an evaluation value, which represents a glossiness of an object to be measured, on the basis of specular reflected light which is reflected by the object to be measured, the method including: acquiring specular reflected light image information in accordance with received light amounts, at predetermined respective pixels, of specular reflected light from a surface of the object to be measured; and calculating the evaluation value representing glossiness of the object to be measured on the basis of the acquired specular reflected light image information.

Accordingly, the fourth aspect, by operations similar to the third aspect, can calculate an evaluation value that attains correspondence with a subjective glossiness even if there are nonuniformities in gloss at the object to be measured, similarly to the third aspect.

It is possible to further acquire, in addition to the specular reflected light image information, diffuse reflected light image information in accordance with received light amounts, at predetermined respective pixels, of diffuse reflected light which, of the light emitted from the light source, has been diffusely reflected by the surface of the object to be measured, and to calculate the evaluation value representing glossiness of the object to be measured on the basis of the acquired specular reflected light image information and the acquired diffuse reflected light image information.

As has been described above, according to the first and second aspects, gloss values of respective pixels are calculated on the basis of received light amounts of the respective pixels in acquired image information and an evaluation value representing glossiness of an object to be measured is calculated on the basis of the calculated gloss values, and thus the first and second aspects have excellent effects in being capable of calculating evaluation values which attain correspondence with subjective glossinesses even when there are inconsistencies in gloss at the objects to be measured.

Furthermore, according to the third and fourth aspects, specular reflected light image information is acquired in accordance with received light amounts at respective pixels of specular reflected light, which has been regularly reflected by a surface of an object to be measured, and an evaluation value representing glossiness of an object to be measured is calculated on the basis of the specular reflected light image information, and thus the third and fourth aspects have excellent effects in being capable of calculating evaluation values which attain correspondence with subjective glossinesses even when there are inconsistencies in glossiness at the objects to be measured.

What is claimed is:

1. A gloss measurement apparatus that emits light from a light source and finds an evaluation value, which represents a glossiness of an object to be measured, on the basis of specular reflected light which is reflected by the object to be measured, the gloss measurement apparatus comprising:

an acquisition component, which acquires image information in accordance with received light amounts, at predetermined respective pixels, of specular reflected light from a surface of the object to be measured;

a pixel gloss value calculation component, which calculates gloss values of the respective pixels on the basis of the received light amounts of the respective pixels of the image information acquired by the acquisition component; and an evaluation value calculation component, which calculates the evaluation value representing glossiness of the object to be measured on the basis of the gloss values calculated by the pixel gloss value calculation component, wherein the gloss value for each of the pixels is calculated by summing values obtained by multiplying respectively different coefficients with each of light amounts of R, G, B for each of the pixels, and the different coefficients are determined by imaging a sample of which the specular gloss value is already known, finding average values of the light amounts of R, G, B of the pixels from the sample, and performing regression analysis using the average values and the known specular gloss value.

2. The gloss measurement apparatus of claim 1, wherein the evaluation value calculation component comprises a distribution calculation component, which calculates a distribution of pixel counts for respective gloss values from the gloss values of the respective pixels, and the evaluation value calculation component identifies a gloss value at which a number of pixels, which is summed from a side of high gloss value in the distribution calculated by the distribution calculation component, reaches a predetermined number, and calculates the evaluation value representing glossiness of the object to be measured on the basis of a total gloss value, the total gloss value being a sum of gloss values of the respective pixels at and above the identified gloss value.

3. The gloss measurement apparatus of claim 1, wherein the evaluation value calculation component comprises an index value calculation component which, on the basis of the gloss values of the respective pixels, calculates an average gloss index value representing an average value of gloss values of all the pixels and a gloss nonuniformity index value representing a degree of occurrence of gloss nonuniformities, and the evaluation value calculation component calculates the evaluation value representing glossiness of the object to be measured by multiplying the average gloss index value and the gloss nonuniformity index value with respective predetermined weighting coefficients, and finding a linear sum of values obtained by the multiplication, such that the evaluation value representing glossiness of the object to be measured increases when the average gloss index value increases and the evaluation value representing glossiness of the object to be measured increases when the gloss nonuniformity index value increases.

4. The gloss measurement apparatus of claim 3, wherein the gloss nonuniformity index value is a value found by dividing a standard deviation value of the gloss values of the respective pixels by the average gloss index value.

5. The gloss measurement apparatus of claim 1, further comprising a correction component, which performs a correction to cause a spatial frequency characteristic of the gloss values of respective pixels which have been calculated by the pixel gloss value calculation component to correspond with a spatial frequency characteristic of human vision, wherein the evaluation value calculation component calculates the evaluation value representing glossiness of the object to be measured on the basis of the gloss values of respective pixels which have been corrected by the correction component.

6. The gloss measurement apparatus of claim 5, wherein the correction component comprises:

a two-dimensional Fourier transform component, which applies a two-dimensional Fourier transformation to the gloss values of the respective pixels which have been calculated by the pixel gloss calculation component, for converting the gloss values to gloss values in a spatial frequency domain;

a multiplication component, which multiplies a predetermined visual transfer function, which corresponds to the spatial frequency characteristic of human vision, with frequency information representing the gloss values of the respective pixels which have been converted to spatial frequency domain gloss values by the two-dimensional Fourier transform component; and a two-dimensional inverse Fourier transform component, which applies a two-dimensional inverse Fourier transformation to results of the multiplication by the multiplication component, for converting the multiplication results to gloss values of respective pixels which are pixels in an image space domain.

7. A gloss measurement method that emits light from a light source and finds an evaluation value, which represents a glossiness of an object to be measured, on the basis of specular reflected light which is reflected by the object to be measured, the method comprising:

acquiring image information in accordance with received light amounts, at predetermined respective pixels, of specular reflected light from a surface of the object to be measured;

calculating gloss values of the respective pixels on the basis of the received light amounts of the respective pixels of the acquired image information; and calculating the evaluation value representing glossiness of the object to be measured on the basis of the calculated gloss values, wherein the gloss value for each of the pixels is calculated by summing values obtained by multiplying respectively different coefficients with each of light amounts of R, G, B for each of the pixels, and the different coefficients are determined by imaging a sample of which the specular gloss value is already known, finding average values of the light amounts of R, G, B of the pixels from the sample, and performing regression analysis using the average values and the known specular gloss value.

8. A storage medium readable by a computer, the storage medium storing a gloss measurement program including instructions which are executable by the computer to perform a function for:

emitting light from a light source; acquiring image information in accordance with received light amounts, at predetermined respective pixels, of specular reflected light which is reflected by an object to be measured; and finding an evaluation value, which represents a glossiness of the object to be measured, on the basis of the acquired image information, the function comprising:

a pixel gloss value calculation step that calculates gloss values of the respective pixels on the basis of the received light amounts of the respective pixels of the acquired image information; and an evaluation value calculation step that calculates the evaluation value representing glossiness of the object to be measured on the basis of the gloss values calculated by the pixel gloss value calculation step, wherein the gloss value for each of the pixels is calculated by summing values obtained by multiplying respectively different coefficients with each of light amounts of R, G, B for each of the pixels, and the different coefficients are determined by imaging a sample of which the specular gloss value is already known, finding average values of the light amounts of R, G, B of the pixels from the sample, and performing regression analysis using the average values and the known specular gloss value.

9. A gloss measurement apparatus that emits light from a light source and finds an evaluation value, which represents a glossiness of an object to be measured, on the basis of specular reflected light which is reflected by the object to be measured, the gloss measurement apparatus comprising:

a specular reflection image information acquisition component, which acquires specular reflected light image information in accordance with received light amounts, at predetermined respective pixels, of specular reflected light from a surface of the object to be measured; and a calculation component, which calculates the evaluation value representing glossiness of the object to be measured on the basis of the specular reflected light image information acquired by the specular reflection image information acquisition component, wherein the gloss value for each of the pixels is calculated by summing values obtained by multiplying respectively different coefficients with each of light amounts of R, G, B for each of the pixels, and the different coefficients are determined by imaging a sample of which the specular gloss value is already known, finding average values of the light amounts of R, G, B of the pixels from the sample, and performing regression analysis using the average values and the known specular gloss value.

10. The gloss measurement apparatus of claim 9, further comprising a diffuse reflection image information acquisition component, which acquires diffuse reflected light image information in accordance with received light amounts, at predetermined respective pixels, of diffuse reflected light which, of the light emitted from the light source, has been diffusely reflected by the surface of the object to be measured, wherein the calculation component calculates the evaluation value representing glossiness of the object to be measured on the basis of the specular reflected light image information acquired by the specular reflection image information acquisition component and the diffuse reflected light image information acquired by the diffuse reflection image information acquisition component.

11. The gloss measurement apparatus of claim 10, wherein the light source emits light including a predetermined incidence angle deviation about an optical axis of the light that is incident at the surface of the object to be measured.

12. The gloss measurement apparatus of claim 10, wherein the calculation component comprises:

a luminance calculation component, which calculates luminances of specular reflected light at respective pixels on the basis of the received light amounts of the respective pixels represented by the specular reflected light image information, and calculates luminances of diffuse reflected light at respective pixels on the basis of the received light amounts of the respective pixels represented by the diffuse reflected light image information;

a first physical quantity calculation component, which calculates a first physical quantity, which corresponds to a luminance difference between specular reflected light and diffuse reflected light, on the basis of the specular reflected light and diffuse reflected light luminances calculated by the luminance calculation component;

a second physical quantity calculation component, which calculates a second physical quantity, which corresponds to nonuniformities in luminance of the specular reflected light, on the basis of the specular reflected light luminances calculated by the luminance calculation component; and an evaluation value calculation component, which calculates the evaluation value representing glossiness of the object to be measured, by multiplying the first physical quantity and the second physical quantity with respective predetermined weighting coefficients and finding a linear sum of values obtained by the multiplication.

13. The gloss measurement apparatus of claim 12, wherein the luminance calculation component divides the received light amounts of the respective pixels represented by the specular reflected light image information by a light-receiving time of the specular received light, and calculates the specular reflected light luminances on the basis of received light amounts per unit time that are obtained by this division, and divides the received light amounts of the respective pixels represented by the diffuse reflected light image information by a light-receiving time of the diffuse received light, and calculates the diffuse reflected light luminances on the basis of received light amounts per unit time that are obtained by this division.

14. The gloss measurement apparatus of claim 13, further comprising a standard surface luminance storage component, which stores a luminance of specular reflected light at a standard surface which is used in measurement of specular gloss, wherein the luminance calculation component calculates the specular reflected light luminances of respective pixels and the diffuse reflected light luminances of respective pixels as values which are normalized in accordance with the luminance of specular reflected light at the standard surface.

15. The gloss measurement apparatus of claim 12, wherein the first physical quantity calculation component calculates an average value of luminances of respective pixels that are at and above a middle value between a maximum luminance and a minimum luminance, of the specular reflected light luminances of respective pixels, and calculates the first physical quantity on the basis of this average value and an average value of the diffuse reflected light luminances of the respective pixels.

16. The gloss measurement apparatus of claim 12, wherein the second physical quantity calculation component applies a two-dimensional Fourier transformation to the specular reflected light luminances at the respective pixels for converting the luminances to luminances in a spatial frequency domain, and divides an integrated value, into which the thus obtained specular reflected light luminances at respective pixels in the spatial frequency domain are integrated over all frequencies, by an average value of the specular reflected light luminances at the respective pixels, for calculating the second physical quantity.

17. The gloss measurement apparatus of claim 10, further comprising:

a stage, which includes a stage surface which retains the object to be measured;

a first translation component, which translates the light source, the specular reflection image information acquisition component and the diffuse reflection image information acquisition component in a predetermined direction, which is parallel with the stage surface; and a second translation component, which translates the stage in a direction intersecting the predetermined direction.

18. The gloss measurement apparatus of claim 17, further comprising an angle alteration component, which alters an angle that is formed between the light source and the specular reflection image information acquisition component about a normal line from an incidence position on the stage surface of the light emitted from the light source.

19. The gloss measurement apparatus of claim 17, further comprising a normal direction movement component, which relatively moves the light source, the specular reflection image information acquisition component and the diffuse reflection image information acquisition component in a normal direction of the stage surface with respect to the stage.

20. The gloss measurement apparatus of claim 17, wherein the stage comprises an electrostatic adherence plate which adheres and retains the object to be measured by electrostatic force.

21. The gloss measurement apparatus of claim 17, further comprising a laser output component, which outputs laser light to an incidence position on the stage surface of the light emitted from the light source.

22. The gloss measurement apparatus of claim 10, further comprising:

a stage, which includes a stage surface which retains the object to be measured;

an r-direction movement component, which moves the light source, the specular reflection image information acquisition component and the diffuse reflection image information acquisition component in a radial r-direction of polar-co-ordinates, an origin point of which is an incidence position on the stage surface of the light emitted from the light source; and a $\theta$-direction rotation component, which rotates the light source, the specular reflection image information acquisition component and the diffuse reflection image information acquisition component in a rotation angle $\theta$ direction.

23. The gloss measurement apparatus of claim 10, wherein the light source comprises:

a halogen fiber light source, which emits light;

a condensing lens, which condenses the light emitted from the halogen fiber light source; and a diffuser, which diffuses the light that has been condensed by the condensing lens.

24. A gloss measurement method that emits light from a light source and finds an evaluation value, which represents a glossiness of an object to be measured, on the basis of specular reflected light which is reflected by the object to be measured, the method comprising:

acquiring specular reflected light image information in accordance with received light amounts, at predetermined respective pixels, of specular reflected light from a surface of the object to be measured; and calculating the evaluation value representing glossiness of the object to be measured on the basis of the acquired specular reflected light image information, wherein the gloss value for each of the pixels is calculated by summing values obtained by multiplying respectively different coefficients with each of light amounts of R, G, B for each of the pixels, and the different coefficients are determined by imaging a sample of which the specular gloss value is already known, finding average values of the light amounts of R, G, B of the pixels from the sample, and performing regression analysis using the average values and the known specular gloss value.

25. The gloss measurement method of claim 24, further comprising acquiring, in addition to the specular reflected light image information, diffuse reflected light image information in accordance with received light amounts, at predetermined respective pixels, of diffuse reflected light which, of the light emitted from the light source, has been diffusely reflected by the surface of the object to be measured, and calculating the evaluation value representing glossiness of the object to be measured on the basis of the acquired specular reflected light image information and the acquired diffuse reflected light image information.

26. A storage medium readable by a computer, the storage medium storing a gloss measurement program including instructions which are executable by the computer to perform a function for emitting light from a light source and finding an evaluation value, which represents a glossiness of an object to be measured, on the basis of specular reflected light which is reflected by the object to be measured, the function comprising:

a storage step, for storing specular reflected light image information at an image information storage component, the specular reflected light image information being acquired in accordance with received light amounts, at predetermined respective pixels, of specular reflected light from a surface of the object to be measured; and an evaluation value calculation step, for calculating the evaluation value representing glossiness of the object to be measured on the basis of the specular reflected light image information which has been stored at the image information storage component, wherein the gloss value for each of the pixels is calculated by summing values obtained by multiplying respectively different coefficients with each of light amounts of R, G, B for each of the pixels, and the different coefficients are determined by imaging a sample of which the specular gloss value is already known, finding average values of the light amounts of R, G, B of the pixels from the sample, and performing regression analysis using the average values and the known specular gloss value.

27. The storage medium of claim 26, wherein the storage step further includes storing diffuse reflected light image information at the image information storage component, the diffuse reflected light image information being acquired in accordance with received light amounts, at predetermined respective pixels, of diffuse reflected light which, of the light emitted from the light source, has been diffusely reflected by the surface of the object to be measured, and the evaluation value calculation step includes calculating the evaluation value representing glossiness of the object to be measured on the basis of the specular reflected light image information and the diffuse reflected light image information which have been stored at the image information storage component.

* * * * *